US012796933B2

United States Patent

Kuranov et al.

(12) United States Patent
(10) Patent No.: US 12,796,933 B2
(45) Date of Patent: Nov. 17, 2026

(54) DEVICES, METHODS, AND SYSTEMS OF FUNCTIONAL OPTICAL COHERENCE TOMOGRAPHY

(71) Applicants: Opticent Health, Evanston, IL (US); Northwestern University, Evanston, IL (US)

(72) Inventors: Roman Kuranov, Morton Grove, IL (US); Hao F. Zhang, Deerfield, IL (US); Cheng Sun, Wilmette, IL (US); Ian Rubinoff, Evanston, IL (US); David Miller, Evanston, IL (US)

(73) Assignees: Opticent Health, Evanston, IL (US); Northwestern University, Evanston, IL (US)

( * ) Notice: Subject to any disclaimer, the term of this patent is extended or adjusted under 35 U.S.C. 154(b) by 409 days.

(21) Appl. No.: 18/361,528

(22) Filed: Jul. 28, 2023

(65) Prior Publication Data

US 2025/0031969 A1 Jan. 30, 2025

(51) Int. Cl.

| | |
|---|---|
| ***A61B 5/00*** | (2006.01) |
| ***G01B 9/02*** | (2022.01) |
| ***G01B 9/02091*** | (2022.01) |
| ***G06T 1/00*** | (2006.01) |

(52) U.S. Cl.

CPC ........ *A61B 5/0066* (2013.01); *G01B 9/02083* (2013.01); *G01B 9/02091* (2013.01); *G06T 1/0007* (2013.01); *G06T 2207/10101* (2013.01)

(58) Field of Classification Search

CPC .............. A61B 5/0066; G01B 9/02083; G01B 9/02091; G06T 2207/10101

See application file for complete search history.

(56) References Cited

PUBLICATIONS

I. Rubinoff et al., "High-Speed Balanced-Detection Visible-Light Optical Coherence Tomography in the Human Retina Using Subpixel Spectrometer Calibration," in IEEE Transactions on Medical Imaging, first published Jan. 28, 2022. (Year: 2022).*

Yusi Miao, Jun Song, Destiny Hsu, Ringo Ng, Yifan Jian, Marinko V. Sarunic, and Myeong Jin Ju, "Numerical calibration method for a multiple spectrometer-based OCT system," Biomed. Opt. Express 13, 1685-1701 (Year: 2022).*

David A. Miller, Roman Kuranov, and Hao F. Zhang, "Adaptive balanced detection spectral domain optical coherence tomography," Biomed. Opt. Express 14, 5208-5222 (Year: 2023).*

Miao et al., "Image-Based Cross-Calibration Method for Multiple Spectrometer-Based OCT," Optica Publishing Group, URL:[https://doi.org/10.1364/OL.468707], Sep. 8, 2022, 5 pages.

(Continued)

*Primary Examiner* — Tarifur R Chowdhury
*Assistant Examiner* — Paul Schnase
(74) *Attorney, Agent, or Firm* — Hanley, Flight & Zimmerman, LLC

(57) ABSTRACT

An optical coherence tomography imaging system is disclosed, including: a light source to generate a radiation beam; a pair of photodetectors to acquire data of the radiation beam; a coupler to direct portions of the beam to a sample arm and a reference arm, the coupler to combine light from the sample arm and the reference arm, the combined light to be split into portions to be detected by the pair of photodetectors; and a processor to measure and compare noise profiles of the data and to generate an image using the data, and the noise profile comparison.

19 Claims, 22 Drawing Sheets

(56) References Cited

PUBLICATIONS

Miao et al., "Numerical Calibration Method for a Multiple Spectrometer-Based OCT System," Biomedical Optics Express, vol. 13, No. 3, Mar. 1, 2022, 17 pages.
Rubinoff et al., "High-Speed Balanced-Detection Visible-Light Optical Coherence Tomography in the Human Retina Using Subpixel Spectrometer Calibration," IEEE Transactions on Medical Imaging, vol. 41, No. 7, Jul. 2022, 11 pages.
Kho et al., "Proactive Spectrometer Matching for Excess Noise Suppression in Balanced Visible Light Optical Coherence Tomography (OCT)," Optics Express, vol. 29, No. 25, Dec. 6, 2021, 18 pages.

* cited by examiner

DEVICES, METHODS, AND SYSTEMS OF FUNCTIONAL OPTICAL COHERENCE TOMOGRAPHY

STATEMENT REGARDING FEDERALLY SPONSORED RESEARCH FOR DEVELOPMENT

This invention was made with government support under grant numbers U01EY033001 and R44EY026466 awarded by the National Institutes of Health. The government has certain rights in the invention.

BACKGROUND

Optical coherence tomography (OCT) is a non-invasive optical imaging technique that produces depth-resolved reflectance imaging of samples through the use of low-coherence interferometry. OCT imaging allows for two-dimensional (2D) and three-dimensional (3D) visualization of structures in a variety of biological and non-biological systems not easily accessible through other imaging techniques. In some instances, OCT may provide a non-invasive, non-contact approach to assess information without disturbing or injuring a target or sample. As such, OCT can be used to image biological tissue, such as retinal or other ocular tissue, using light (e.g., near-infrared, visible light, etc.) emitted at a broad range of frequencies. The interference of light occurs when the optical paths of the light reflected from a sample matches with an optical path of reference light within micrometer-scale precision (e.g., low-coherence). However, slow imaging speeds, cost-prohibitive light sources, and difficulty in calibration have hindered effective use of OCT. A need exists for improved OCT systems and methods of use.

BRIEF DESCRIPTION OF THE DRAWINGS

A better understanding of the features and advantages of this disclosure will be obtained by reference to the following detailed description that sets forth illustrative examples, in which the principles of a device of this disclosure are utilized, and the accompanying drawings.

Figure 1:
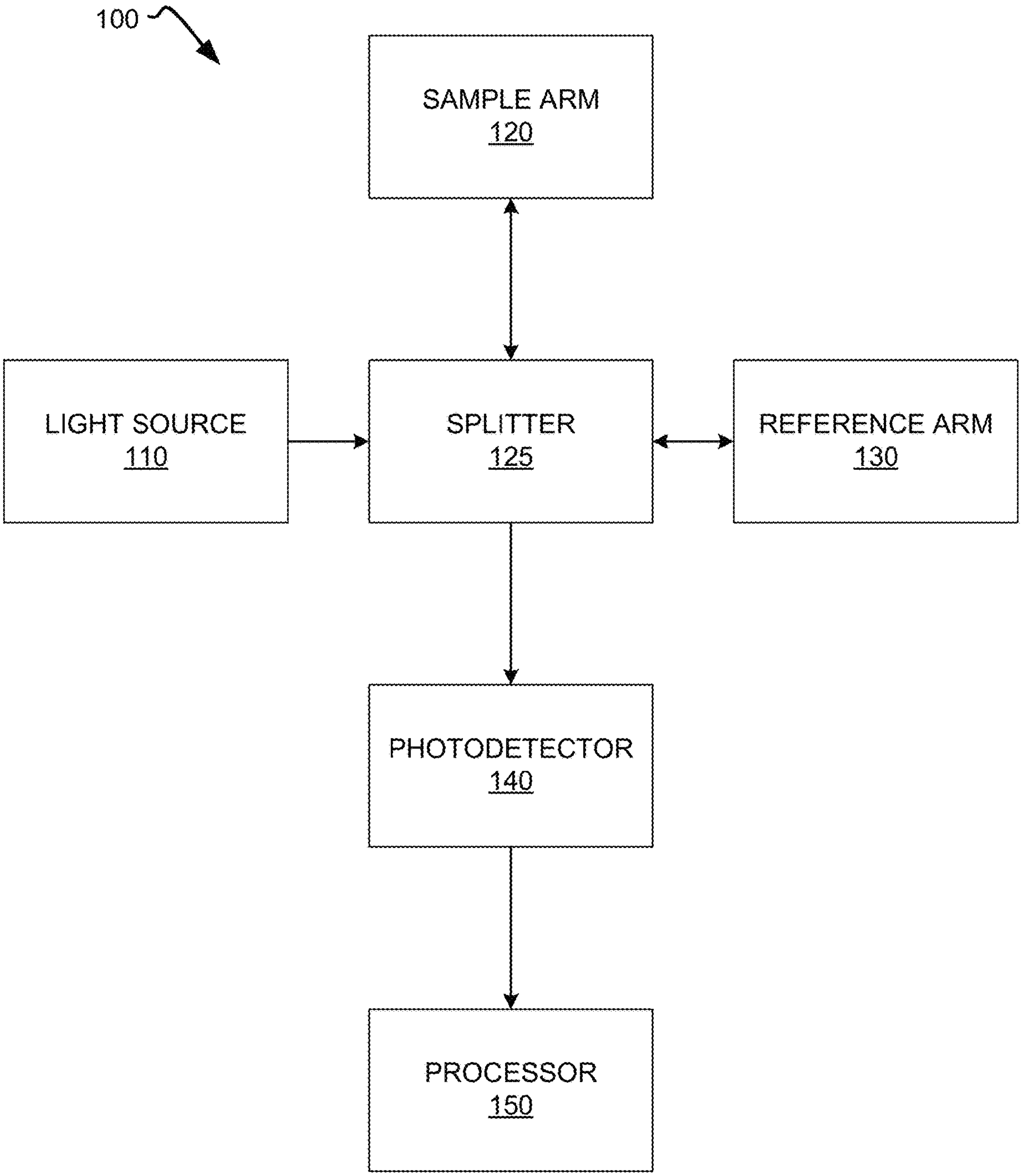
FIG. 1 illustrates an example OCT apparatus.

The following detailed description of certain examples of the present invention will be better understood when read in conjunction with the appended drawings. For the purpose of illustrating the invention, certain examples are shown in the drawings. It should be understood, however, that the present invention is not limited to the arrangements and instrumentality shown in the attached drawings.

DETAILED DESCRIPTION OF THE DISCLOSURE

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical, and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

In general, the same reference numbers will be used throughout the drawing(s) and accompanying written description to refer to the same or like parts. The figures are not to scale.

Definitions

Throughout the specification and claims, the following terms take the meanings explicitly associated herein, unless the context clearly dictates otherwise.

As used in this patent, stating that any part (e.g., a layer, film, area, region, or plate) is in any way on (e.g., positioned on, located on, disposed on, or formed on, etc.) another part, indicates that the referenced part is either in contact with the other part, or that the referenced part is above the other part with one or more intermediate part(s) located therebetween.

As used herein, connection references (e.g., attached, coupled, connected, and joined) may include intermediate members between the elements referenced by the connection reference and/or relative movement between those elements unless otherwise indicated. As such, connection references do not necessarily infer that two elements are directly connected and/or in fixed relation to each other. As used herein, stating that any part is in "contact" with another part is defined to mean that there is no intermediate part between the two parts.

When introducing elements of various embodiments of the present disclosure, the articles "a," "an," "the," and "said" are intended to mean that there are one or more of the elements. As used herein, singular references (e.g., "a", "an", "first", "second", etc.) do not exclude a plurality. The term "a" or "an" object, as used herein, refers to one or more of that object. The terms "a" (or "an"), "one or more", and "at least one" are used interchangeably herein. Furthermore, although individually listed, a plurality of means, elements, or method actions may be implemented by, e.g., the same entity or object. Additionally, although individual features may be included in different examples or claims, these may possibly be combined, and the inclusion in different examples or claims does not imply that a combination of features is not feasible and/or advantageous.

The terms "comprising," "including," and "having" are intended to be inclusive and mean that there may be additional elements other than the listed elements. That is, "including" and "comprising" (and all forms and tenses thereof) are used herein to be open-ended terms. Thus, whenever a claim employs any form of "include" or "comprise" (e.g., comprises, includes, comprising, including, having, etc.) as a preamble or within a claim recitation of any kind, it is to be understood that additional elements, terms, etc., may be present without falling outside the scope of the corresponding claim or recitation. As used herein, when the phrase "at least" is used as the transition term in, for example, a preamble of a claim, it is open-ended in the same manner as the term "comprising" and "including" are open-ended. The term "and/or" when used, for example, in a form such as A, B, and/or C refers to any combination or subset of A, B, C such as (1) A alone, (2) B alone, (3) C alone, (4) A with B, (5) A with C, (6) B with C, or (7) A with B and with C. As used herein in the context of describing structures, components, items, objects, and/or things, the phrase "at least one of A and B" is intended to refer to implementations including any of (1) at least one A, (2) at least one B, or (3) at least one A and at least one B. Similarly, as used herein in the context of describing structures, components, items, objects and/or things, the phrase "at least one of A or B" is intended to refer to implementations including any of (1) at least one A, (2) at least one B, or (3) at least one A and at least one B. As used herein in the context of describing the performance or execution of processes, instructions, actions, activities, and/or steps, the phrase "at least one of A and B" is intended to refer to implementations including any of (1) at least one A, (2) at least one B, or (3) at least one A and at least one B. Similarly, as used herein in the context of describing the performance or execution of processes, instructions, actions, activities and/or steps, the phrase "at least one of A or B" is intended to refer to implementations including any of (1) at least one A, (2) at least one B, or (3) at least one A and at least one B.

Unless specifically stated otherwise, descriptors such as "first," "second," "third," etc., are used herein without imputing or otherwise indicating any meaning of priority, physical order, arrangement in a list, and/or order in any way, but are merely used as labels and/or arbitrary names to distinguish elements for ease of understanding the disclosed examples. In some examples, the descriptor "first" may be used to refer to an element in the detailed description, while the same element may be referred to in a claim with a different descriptor such as "second" or "third." In such instances, it should be understood that such descriptors are used merely for identifying those elements distinctly that might, for example, otherwise share the same name.

As used herein, "approximately" and "about" modify their subjects/values to recognize the potential presence of variations that occur in real-world applications. For example, "approximately" and "about" may modify dimensions that may not be exact due to manufacturing tolerances and/or other real-world imperfections as will be understood by persons of ordinary skill in the art. For example, "approximately" and "about" may indicate such dimensions may be within a tolerance range of +/−10% unless otherwise specified in the below description. As used herein "substantially real-time" refers to the occurrence in a nearly instantaneous manner recognizing there may be real-world delays for computing time, transmission, etc. Thus, unless otherwise specified, "substantially real-time" refers to real-time +/−1 second.

Ranges can be expressed herein as from "about" one particular value, and/or to "about" another particular value. When such a range is expressed, another example includes from one particular value to another particular value. Similarly, when values are expressed as approximations, by use of the antecedent "about," it will be understood that the particular value forms another example. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5.

As used herein, the phrase "in communication," including variations thereof, encompasses direct communication and/or indirect communication through one or more intermediary components, and does not require direct physical (e.g., wired) communication and/or constant communication, but rather additionally includes selective communication at periodic intervals, scheduled intervals, aperiodic intervals, and/or one-time events.

As used herein, the terms "system," "unit," "module," "engine," etc., may include a hardware and/or software system that operates to perform one or more functions. For example, a module, unit, or system may include a computer processor, controller, and/or other logic-based device that performs operations based on instructions stored on a tangible and non-transitory computer-readable storage medium, such as a computer memory. Alternatively, a module, unit, engine, or system may include a hard-wired device that performs operations based on hard-wired logic of the device. Various modules, units, engines, and/or systems shown in the attached figures may represent the hardware that operates based on software or hardwired instructions, the software that directs hardware to perform the operations, or a combination thereof.

As used herein, "processor circuitry" is defined to include (i) one or more special purpose electrical circuits structured to perform specific operation(s) and including one or more semiconductor-based logic devices (e.g., electrical hardware implemented by one or more transistors), and/or (ii) one or more general purpose semiconductor-based electrical circuits programmable with instructions to perform specific operations and including one or more semiconductor-based logic devices (e.g., electrical hardware implemented by one or more transistors). Examples of processor circuitry include programmable microprocessors, Field Programmable Gate Arrays (FPGAs) that may instantiate instructions, Central Processor Units (CPUs), Graphics Processor Units (GPUs), Digital Signal Processors (DSPs), XPUs, or microcontrollers and integrated circuits such as Application Specific Integrated Circuits (ASICs). For example, an XPU may be implemented by a heterogeneous computing system including multiple types of processor circuitry (e.g., one or more FPGAs, one or more CPUs, one or more GPUs, one or more DSPs, etc., and/or a combination thereof) and application programming interface(s) (API(s)) that may assign computing task(s) to whichever one(s) of the multiple types of processor circuitry is/are best suited to execute the computing task(s).

In addition, it should be understood that references to "one embodiment" or "an embodiment" of the present disclosure are not intended to be interpreted as excluding the existence of additional embodiments that also incorporate the recited features.

Example OCT Systems and Methods

Optical coherence tomography (OCT) is a non-invasive imaging technology that uses the interference of backscattered broadband light with reference to reconstruct high-resolution, three-dimensional images of biological tissues. In medicine, for example, OCT applications include, but are not limited to, non-invasive diagnosis of diseases in the retina of the eye, interventional cardiology treatment and assessment, and diagnostics of skins lesion for dermatology. For example, since an eye is an optically transparent media until light reaches the layered scattering structure of the retina, OCT is used in ophthalmology clinics for diagnosis and monitoring of retinal diseases including diabetic retinopathy, age-related macular degeneration (AMD), and glaucoma. Most clinical OCT devices operate using near-infrared (NIR) light. However, shifting the illumination wavelengths to the visible-light range can achieve higher axial resolution and enable unique tissue contrast and functional assessments. For example, visible-light OCT (vis-OCT) has been applied to visualize Bruch's membrane, inner plexiform layer sub-layers, and quantify oxygen saturation in individual blood vessels. However, the broader adoption of vis-OCT by the research and clinical communities has been hindered by slow imaging speeds and cost-prohibitive light sources.

The reduced speed of vis-OCT is associated with the high level of the relative intensity noise (RIN) of the non-linear supercontinuum lasers used as a vis-OCT source. As used herein, RIN can be used to describe the intensity fluctuation of the wavelength-dependent broadband light source itself (rather than signal intensity fluctuation that is also influenced by detector and digitization) for broadband OCT sources including NIR. As used herein, excess photon noise is considered a part of a broader definition of the RIN.

In OCT, RIN can significantly degrade a signal-to-noise ratio (SNR) of an image. Such SNR degradation limits image quality, degrades image parameter measurement accuracy, and reduces data acquisition rate. High-speed image acquisition is critical for mitigating subject-dependent motion artifacts. As such, RIN suppression is essential for achieving high-quality images.

In a single spectrometer visible-light spectral domain OCT (vis-SD-OCT), a partial reduction of the RIN can be achieved by increasing a repetition rate of picosecond or tens of picosecond pulses of a supercontinuum source. However, this reduction does not fully mitigate RIN and dramatically increases the complexity (and associated price) of the source.

Additionally, in SD-OCT, interference fringes are spectrally dispersed over a linear array of detectors, where each detector element (pixel) converts narrow bandwidth light centered at specific wavelengths into an electrical signal. For effective balanced detection, the recorded spectra must be perfectly co-registered in wavelength to ensure full subtraction of the wavelength-dependent RIN. In other words, the individual pixels of one spectrometer camera must detect the same wavelengths as the corresponding pixels on the other camera. The signals produced by the corresponding pixels are subtracted to double the detected interference signal and subtract RIN. Unfortunately, due to imperfections in the lenses and small discrepancies in the machining and alignment of the spectrometers, it is impractical to achieve perfect spectral matching between the spectrometers. Such imperfections reduce RIN suppression due to poor spectral matching of the wavelength-dependent RIN components.

Balanced detection OCT (BD-OCT) provides suppression of RIN through addition of a second detector that simultaneously measures interference signals with a π phase shift between the detectors. Subtracting two simultaneously detected fringes sums π shifted interference signals while removing the common noise between detectors, which contains RIN and autocorrelation terms. However, uncorrelated noises (e.g., shot, thermal, and digitization noises) from each of the individual spectrometers are increased in accordance with:

$$n_{\Sigma} = \sqrt{n_{sp1}^2 + n_{sp2}^2}. \qquad \text{(Eq. 1)}$$

In Equation 1, $n_{sp1}$ and $n_{sp2}$ are noises from spectrometer 1 and 2 respectively, and $n_{\Sigma}$ is non-common noise after balanced detection.

BD-OCT is straightforward for swept-source OCT (SS-OCT) and time domain OCT (TD-OCT), in which single-element detectors are used and, therefore, spectral components are automatically spectrally and temporally correlated in SS-OCT and are integrated in TD-OCT. Although BD-OCT for spectrometer-based, spectral domain OCT (SD-OCT) was proposed previously, the full benefits of BD-OCT were not fully realized due to poor temporal and spectral correlation of RIN components matching. Certain examples provide substantially improved BD performance in SD-OCT through precise temporal and spectral matching of RIN noise components between two spectrometers to ensure optimal or otherwise improved removal of common noise with short correlation values in time and wavelength domains.

Certain examples achieve temporal correlation using a trigger for frame grabbers associated with matching spectrometers. For efficient RIN suppression, wavelength matching between spectrometers is achieved with precision exceeding a wavelength shift between any two neighboring pixels of the spectrometer, which involves matching with subpixel accuracy. For example, a three-fold reduction in RIN suppression can occur by introducing a 1-pixel shift between the spectrometer pair. Subpixel matching can achieve >20 dB RIN suppression and can be performed in both hardware and software, for example. Hardware matching is achieved through alignment of the spectrometer pair with guidance from a correlation map that can be generated from a RIN- or signal-dominated dataset. Subpixel mechanical matching of the spectrometers is challenging. Moreover, environmental vibrations and drift may lead to misalignment with time. Fiber reconnection to an input of a spectrometer cannot be made with repeatable spectral precision to guarantee that subpixel wavelength matching is preserved. Thus, software-based matching is performed using an interpolation vector or transformation matrix that interpolates pixels from one spectrometer to another. Selection of this interpolation vector or transformation matrix is used to maximize or other improve RIN suppression.

Interpolation vector selection from a spectrometer pair can be performed using either a RIN- or signal-dominated dataset, for example. A RIN-dominated dataset is synchronously acquired from a spectrometer pair after decreasing a spectrometer camera amplification level and an integration time of both cameras to their minimal values to increase the optical power incident on spectrometer camera, which increases a dominance of the RIN over other noise types. The RIN noise dominates because the RIN noise is proportional to the light power squared, while shot noise is linearly proportional to the light power, and thermal and digitization noises are not dependent on the light power. Wavelength-dependent temporal noise fluctuations from the RIN-dominated dataset are used to identify a map of the closest wavelength-matched pixels between the spectrometer pair and subpixel matching achieved by oversampling and interpolating of the initial map, for example. Although robust, these methods require pre-calibrated measurements and light sources with largely dominating RIN noise.

A signal-dominated dataset includes an OCT B-scan containing an interference signal that is synchronously acquired from a spectrometer pair. Temporal signal fluctuations can then be used to match the spectrometer pair using a correlation matrix. However, this technique involves additional finely-tuned post-processing steps and manual selection of the correlation matrix contour points to generate an interpolation vector. In general, this technique performs best when an unbalanced SNR from each of the matching spectrometers is maximized. As mentioned above, interpolation vector selection methods rely on the long-term stability of the spectrometer pair, which may be influenced by vibration, temperature fluctuations, and/or variations in fiber insertion angle, for example. Such instabilities require routine recalibration to ensure optimal RIN suppression stays intact over time. Thus, there is a need for an interpolation vector selection method that can be performed on any synchronously acquired dataset from a spectrometer pair, regardless of RIN or signal level.

As such, certain examples provide an adaptive approach for subpixel matching that can be applied to any OCT image, regardless of its RIN or signal level, referred to as adaptive balancing. The adaptive balancing can be applied to both vis- and NIR-OCT. Although NIR OCT utilizes less noisy light sources than vis-OCT, balanced detection can benefit NIR SD-OCT as well.

To address the spectral pixel mismatch between spectrometers, methods have been proposed to mechanically and computationally optimize the pixel mapping through careful alignment and calibration procedures, which lead to effective noise cancellation and signal improvement. Such techniques hinge on accurate calibration for proper operation. An example calibration process uses a mirror placed in a sample arm to acquire interference fringes at several different depth positions. Next, remapping between pixels of a conjugate spectrometers is achieved by optimizing the coefficients of a third order polynomial fit to the mapping between the spectrometers. The coefficients are optimized until the mean-squared error (MSE) between the interferograms captured by the two spectrometers is minimized. Setting the mirror to different depth positions makes the algorithm less sensitive to the depth position of the layers of interest in the sample. Such a procedure needs to be done after or before imaging and requires qualified engineers or technicians to perform it. Careful placement and adjustment of the sample arm mirror and optics to detect enough light without saturation and spectral distortion requires professional optical skills to perform such a procedure. Additionally, such a procedure cannot address variations of the precise system parameters during the scans and is impractical between the scans due to time restrictions allowed by a patient.

Certain examples eliminate the need for prior knowledge of the OCT signal for calibration or the requirement for careful calibration by engineers. Instead, certain examples provide an optimization routine to iteratively change the coefficients of a polynomial mapping between spectrometers. The coefficients are optimized until the variance and amplitude of the DC term, where the RIN dominates in the processed images, are minimized. As such, certain examples satisfy the need for a pixel-matching method that does not require calibration or hardware alignment by experienced professionals and can be applied to any OCT signal acquired by a balanced detection system.

Example OCT Systems

FIG. 1 illustrates an example high-level schematic of an OCT system 100. The example system 100 includes a light source 110, a sample arm 120, a splitter 125, a reference arm 130, a photodetector 140, and a processor 150. As shown in the example of FIG. 1, the light source 110 (e.g., a laser, a wideband light source, a wideband spatially coherent light source, a supercontinuum laser light source, a lamp, superluminescent diode (SLD), amplified spontaneous emission (ASE) light source, a light-emitting diode (LED), etc.) generates a beam of radiation (e.g., a beam of light) that is split using an optical beam splitter 125 into a portion reaching the sample arm 120 and a portion reaching the reference arm 130. Light backscattered from the sample arm 120 and light transmitted from the reference arm 130 is received by the photodetector 140 (e.g., a spectrometer, a pair of spectrometers, etc.). The photodetector 140 records interference fringes, for example, from the received light and routes recorded information to the processor 150 for processing.

Figure 2:
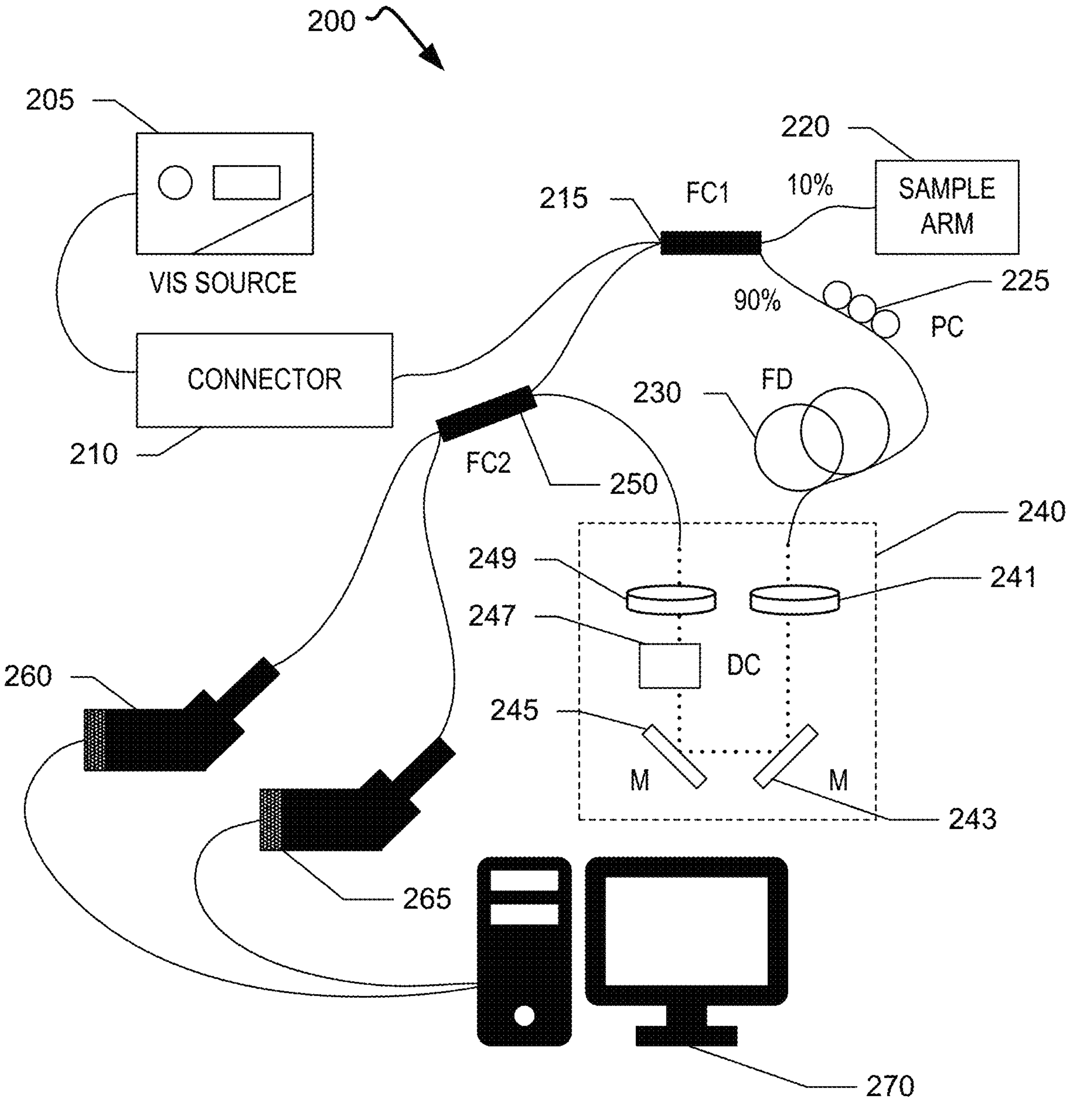
FIG. 2 illustrates an example configuration of a vis-OCT system.

More specifically, FIG. 2 illustrates an example configuration of a BD-vis-OCT system 200. In the example of FIG. 2, a visible light source 205 (e.g., a laser, a wideband light source, a lamp, a light-emitting diode (LED), etc.) provides light (e.g., visible light, NIR light, etc.) to a cable or conduit 210 (e.g., a unit to launch light from a photonic crystal fiber output of a supercontinuum laser and filtering spectrum to a desired bandwidth and shape, connector, etc.), which filters and/or otherwise adjusts the light. The adjusted light is provided via a fiber coupler (FC) 215 (e.g., a fiber-based beam splitter) to i) a sample arm 220 and ii) via a polarization controller (PC) 225 and a fiber delay 230 to a reference arm 240. In an example, 10% of an output of the FC 215 is provided to the sample arm 220, and 90% of the output is provided to the reference arm 240.

As shown in the example of FIG. 2, the reference arm 240 includes a first collimating lens (CL) 241, which provides, in a translation stage (TS), the light to a first mirror (M) 243, which reflects the light to a second mirror 245. Light reflected off of M 245 passes through a dispersion compensation (DPC) glass 247 and then through a second CL 249.

Light backscattered from the sample arm 220 and transmitted from the reference arm 240 are coupled via a FC 250, which provides the combined light to a first photodetector 260 (e.g., a first spectrometer) and a second photodetector 265 (e.g., a second spectrometer). In certain examples, the combined light has an interference with contributions from the sample arm 220 and the reference arm 240. In other examples, the combined light does not have an interference with contribution from the sample arm 220 and the reference arm 240. Instead, the combined light contains noise. In some examples, the combined light does not have an interference with contribution from the sample arm 220 and the reference arm 240 and only contains light from the light source 205.

In certain examples, the light from the FC 250 is split evenly between the first photodetector 260 and the second photodetector 265. Both photodetectors 260, 265 record the interference fringes of their respective portion of the received light. The photodetectors 260, 265 separately acquire the respective portion of the light. The photodetectors 260, 265 can be synchronized in acquisition of the light, for example.

The photodetectors 260. 265 provide recorded information to a processor 270. The processor 270 processes the information to measure and compare a noise profile of the first photodetector 260 and the second photodetector 265 in generating an image.

In certain examples, comparing the noise profile involves measuring the noise profile. Measuring the noise profile includes measurement of a relationship established mathematically to correlate noise signals that have been independently acquired from the first photodetector 260 and the second photodetector 265. In certain examples, a mathematical correlation is applied to the noise signal acquired by the first photodetector 260 and mapped to the second photodetector 265 before a linear transform (e.g., a Fourier transform, etc.) is applied. In certain examples, the photodetectors 260, 265 acquire spectra of the noise in the noise signal. In certain examples a difference between a first noise profile received by the first photodetector 260 and a second noise profile received by the second photodetector 265 is determined and used to generate the image.

In certain examples, measuring and comparing the noise profile includes reducing an intensity of the light source 205 to a threshold value such that the signal acquired from the first photodetector 260 and/or the second photodetector 265 has a certain percentage of noise (e.g., at least 10%, 20%, 30% 40%, 50%, 60%, 70%, 80%, 90%, 95%, 99% etc.). In certain examples, measuring and comparing the noise profile includes generating a calibration map between the first photodetector 260 and the second photodetector 265, matching and identifying constant elements in the calibration map, and subtracting the constant elements from the signal used to generate the resulting ocular image. For example, a calibrated mapping between the first photodetector 260 and the second photodetector 265 is based on pixel elements, sub-pixel elements, etc.

In certain examples, constant elements from the signal used to generate the image are combined to reduce noise. In certain examples, the combination of constant elements from the signal used to generate the image provides noise reduction. In certain examples, the constant elements are combined using a mathematical correlation. The mathematical correlation of the constant elements from the signal used to generate the image can be a sub-pixel correction, for example. In certain examples, the mathematical correlation is at a resolution of less than one pixel for either the first photodetector 260 or the second photodetector 265.

In certain examples, a calibration map is generated based on the mathematical correlation. The calibration map can be generated for one or more image acquisitions, for example. The calibration map can be generated from the noise part of the signal after linear transform, for example. The calibration map generated from the image can be approximated as a polynomial function of the constant detector elements, for example. In certain examples, coefficients of the polynomial function characterize an offset and spacing between constant detector elements. The coefficients can be modified by computational optimization, for example. The computational optimization changes coefficients to minimize a cost function, for example. The cost function can be a measure of an average intensity and noise profile of the image from a selected depth or whole image, for example.

In certain examples, measuring and comparing the noise profile of the first photodetector 260 and the second photodetector 265 is performed before the generation of an image. In certain examples, measuring and comparing the noise profile of the first photodetector 260 and the second photodetector 265 is performed to the generation of an image. In certain examples, measuring and comparing the noise profile of the first photodetector 260 and the second photodetector 265 is performed after the generation of an image. In certain examples, measuring and comparing the noise profile of the first photodetector 260 and the second photodetector 265 is performed simultaneously with the generation of an image.

In certain examples, measuring and comparing the noise profiles of the first photodetector 260 and the second photodetector 265 further includes matching a bandwidth of the first photodetector 260 with a bandwidth of the second photodetector 265 and shifting the pixels in each of the first and second photodetectors 260, 265 from left to right. In certain examples, measuring and comparing the noise profiles of the first photodetector 260 and the second photodetector 265 further includes linear and/or non-linear matching.

In certain examples, measuring and comparing the noise profiles of first photodetector 260 and the second photodetector 265 further includes measurement of intrinsic and/or extrinsic noise signals. In certain examples, the intrinsic noise signals further include any signal contribution from the light source 205 and/or other components of the system 200. In certain examples, the extrinsic noise signals further include any noise signals contributed from signals externally applied to the system 200. In certain examples, the noise signals include fluctuations in signal.

In certain examples, the FC 250 and associated optics to direct and combine light are fiber optics. In certain examples, the FC 215 is fiber optic. In certain examples, the FC 250 and associated optics to direct and combine light are a combination of bulk optics and fiber optics. In certain examples, the FC 215 are a combination of bulk optics and fiber optics. In certain examples, measuring and comparing the noise profiles of the first photodetector 260 and the second photodetector 260 is achieved through the use of a spectral filter. In certain examples, the photodetectors 260, 265 are two independent units. In certain examples, the photodetectors 260, 265 are combined in a single unit.

Figure 3:
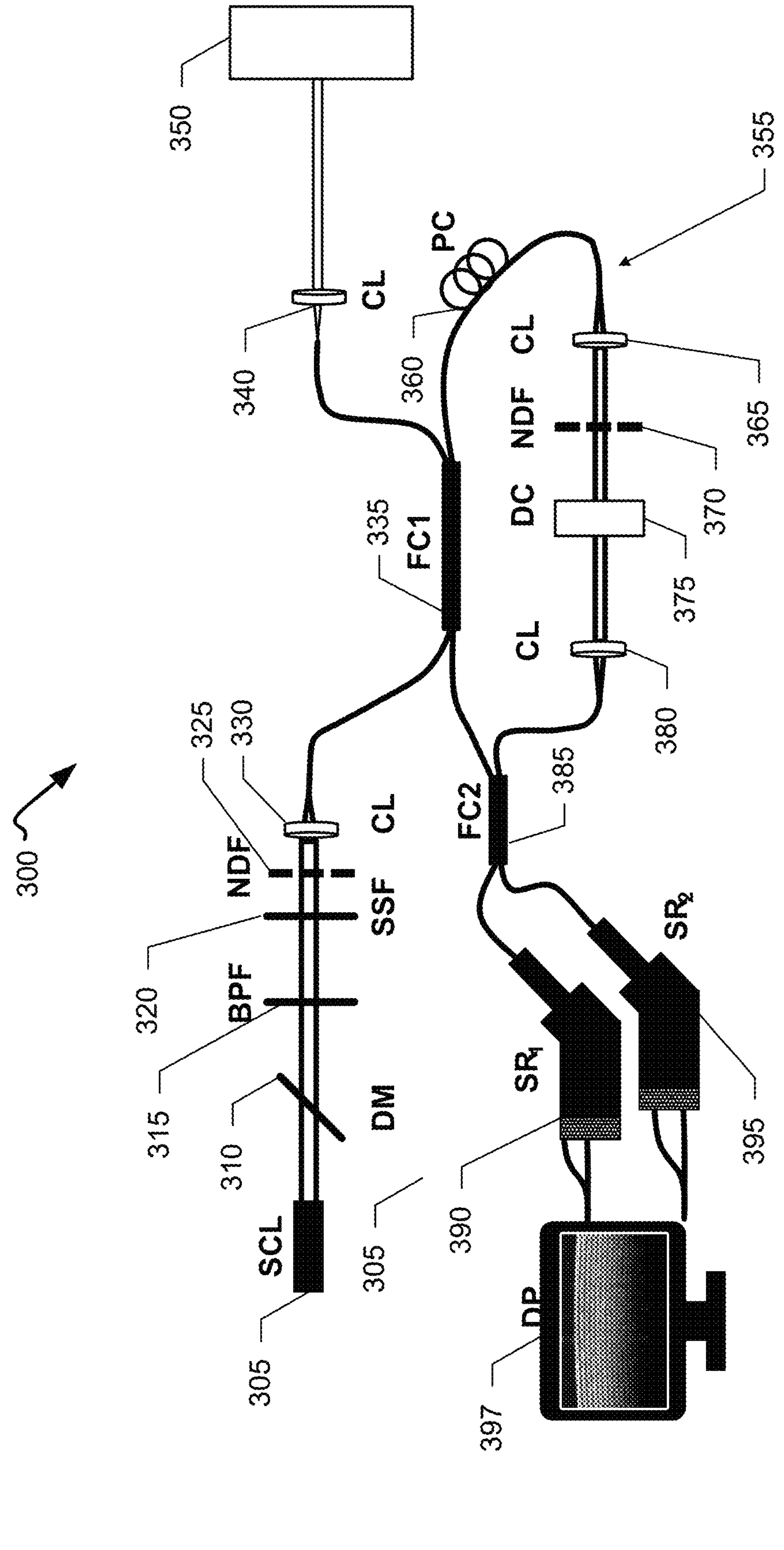
FIG. 3 illustrates an example BD-vis-OCT system.

FIG. 3 illustrates an example BD-vis-OCT system 300 for retinal imaging based on a single mode. The example system 300 includes a laser 305 (e.g., a supercontinuum (SC) laser such as a SuperK series laser, NKT Photonics, Denmark). A beam from the laser 305 is filtered by a short-pass dichroic mirror (DM) 310 (e.g., a DMSP650; Thorlabs, NJ), a bandpass filter (BPF) 315 (e.g., an FF01-560/94-25, Semrock, NY), and a spectral shaping filter (SSF) 320 (e.g., Hoya B-460, Edmund Optics, NJ). A power of the laser beam is controlled using a variable neutral density filter (NDF) wheel 325 (e.g., NDC-25C-2M, Thorlabs) and filtered through a CL 330. The filtered SC laser light is coupled into a single-mode fiber-based coupler (FC) 335 (e.g., TW560R2A2, Thorlabs). The FC 335 splits the light into two portions, such as 10% and 90%. The 10% output of the FC 335 is delivered through a CL 340 to a sample arm 350.

For example, the CL 340 collimates a 1.5 mm diameter beam onto a 2 axis, 5 mm galvanometric scanning mirror (GM) 352 (e.g., 6210 h, Novanta, MA). A two-lens blocks Keplerian telescopic system (KT) 354 with a 3:1 magnification ratio delivers light to a sample 356 (e.g., a tape phantom (TP), other artificial sample, human or animal eye, etc.).

The 90% output of the FC 335 is delivered to a transmission-mode reference arm 355. The reference arm 355 includes a PC 360, a variable NDF 365, and a dispersion compensation glass (DPC) 375, with a CL 380. Backscattered light from the sample arm 350 is input to a first port of an FC 385 (e.g., TW560R5A2, Thorlabs), and transmitted light from the reference arm 355 is input to a second port of the FC 385. The FC 385 can couple the two light inputs 50:50, for example. The splitting ratio of the FC 385 can be controlled to better match light detection by the two spectrometers. Control can be achieved for example by varying the temperature of the FC 385. Output ports of the single-mode FC 385 are connected to a first spectrometer (SR) 390 and a second spectrometer 395 (e.g., Blizzard SR, Opticent Health, IL). The spectrometers 390, 395 record interference fringes of the light. For example, the SR 390 has a wavelength detection range of 509 nm to 614 nm, and the SR 395 has a detection range of 506 nm to 612 nm. Output of the SR 390, 395 is provided to a processor 397.

Figure 4:
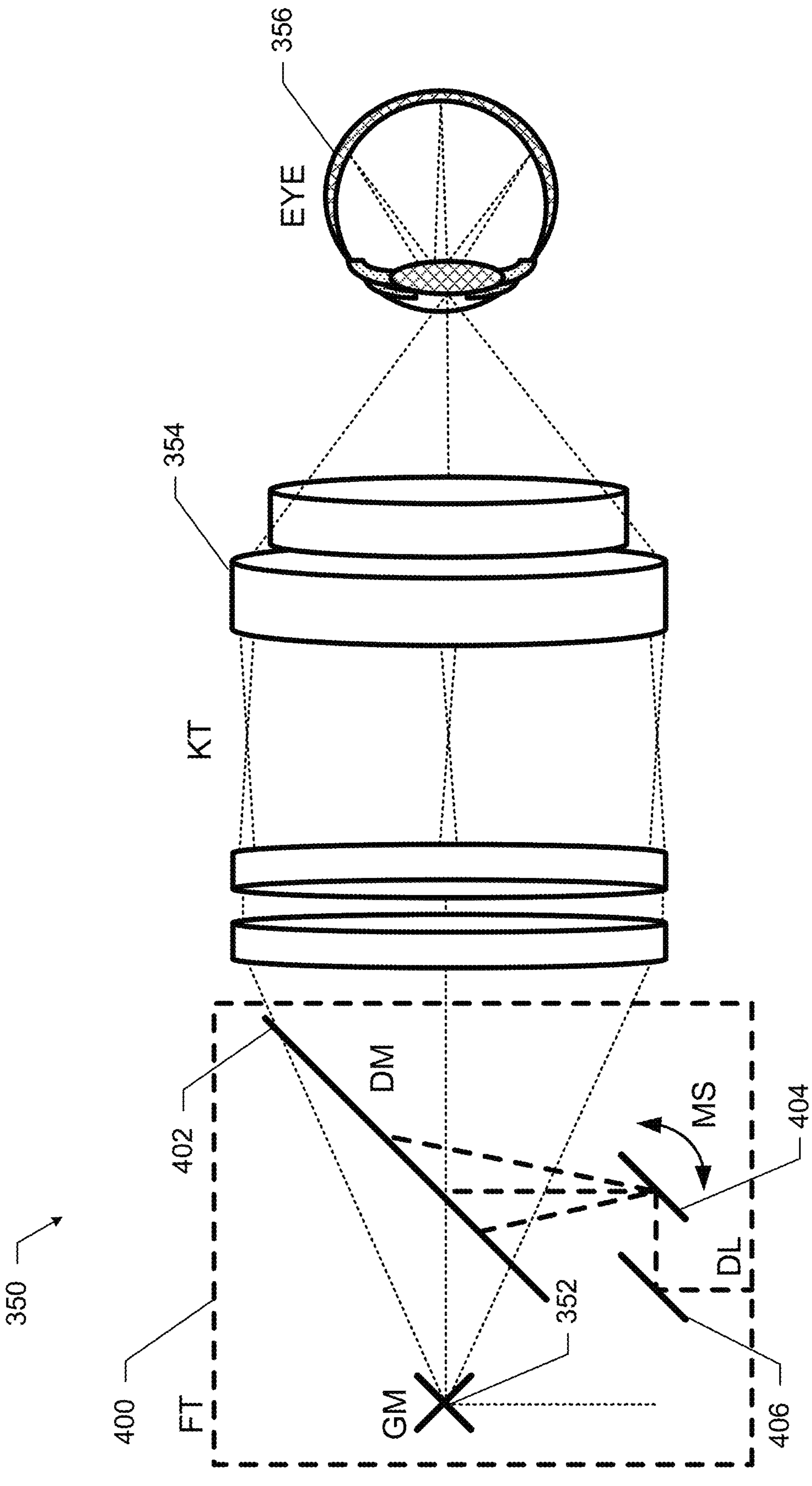
FIG. 4 provides a more detailed view of the sample arm of the example system of FIG. 3.

FIG. 4 provides a more detailed view of the example sample arm 350 of FIG. 3. As shown in the example of FIG. 4, the GM 352 (e.g., a 1D or 2D galvo mirror) reflects broadband light from the CL 340 at different angle positions into the KT 354. The KT 354 delivers light to the sample 356 (e.g., an eye, etc.), and backscattered light is provided back through the GM 352, for example. A fixation target (FT) system 400 provides a fixation image to the subject to enable imaging of different retinal features by rotating the subject's eye. A diode laser (DL LPS-675-PC, Thorlabs) of 670 nm wavelength illuminates a micro-electromechanical system (MEMS) mirror scanner (MS 404). The MS 404 scans a pre-programmed pattern on dichroic mirror (DM, 3414-666, Alluxa) 402, which reflects light from the FT 400 through KT 354. The position of the pre-programmed pattern on DM 402 can be changed to guide the subject eye to different imaging angles, for example. As such, turning mirrors 406 and 404 guide target laser light to fix position of the eye, and the dichroic mirror 402 combines OCT light (transmitting it) with target laser light (reflecting it).

Figure 5:
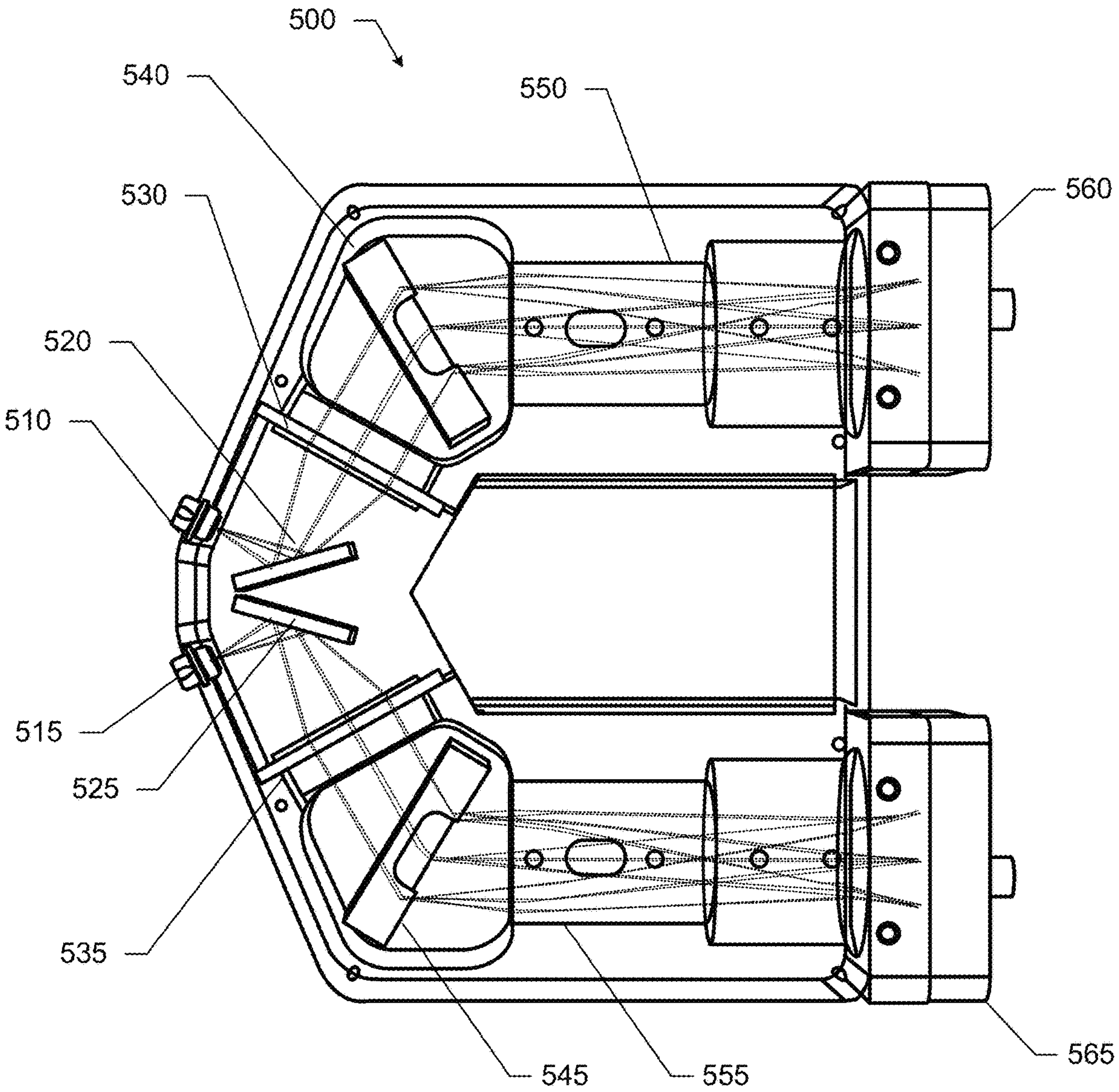
FIG. 5 illustrates an example combination of spectrometers into a single device.

In certain examples, the spectrometers 260-265, 390-395 can be combined into a single unit. FIG. 5 illustrates an example combination of spectrometers into a single device 500. The example apparatus 500 of FIG. 5 includes a pair of fiber adapters 560, 565, which serve as an interface to receive light from the FC 250, 385 implemented as part of the example apparatus 500. Light input through the adapters 560, 565 impacts a pair of turning mirrors 520, 525, which direct the light along the optical path within the apparatus 500. A collimator 530, 535 prepares the light by making the respective light parallel and directed toward a grating 540, 545 (e.g., a diffraction grating, etc.). The collimator 530, 535 guides or directs the light to pass through the grating 540, 545 rather than diverge and scatter off of the grating 540, 545. After passing through the grating 540, 545, the light is processed by a respective camera lens module 550, 555, which prepares the light for impact on a charge-coupled device (CCD) or CMOS camera 560, 565. Each pixel of the CCD 560, 565 receives light at a narrow band and converts that light into a digital signal representative of the image. The light can represent fringes, for example. The digital signal from each CCD 560, 565 can be provided to the processor 270, 397 for further analysis, for example.

Figure 6:
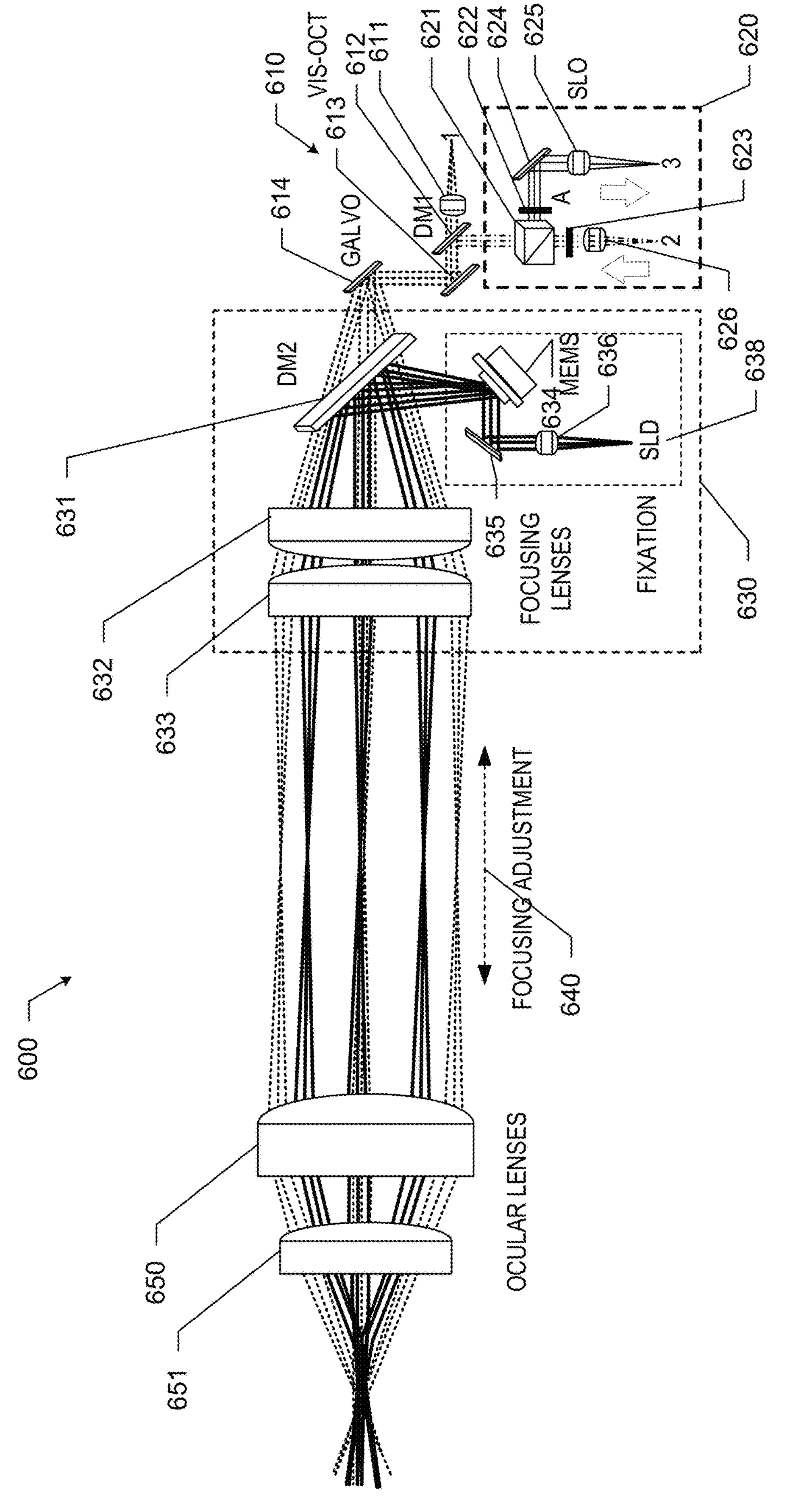
FIG. 6 illustrates an example integrated NIR-SLO and vis-OCT system.

Scanning laser ophthalmoscopy (SLO) uses a collimated laser beam to image the eye. As such, a system can integrate aspects of SLO and vis-OCT for ocular imaging. FIG. 6 illustrates an example integrated NIR-SLO, vis-OCT system 600 for internal eye fixation and imaging. The example sample arm system 600 includes light from a vis-OCT system 610, as delivered by a sample arm of a FC 215 or 335, in which a beam of light 1 is conveyed via a first CL 611 to a first DM (DM1) 612. The DM1 612 allows a first portion of the light (vis-OCT) to pass through to a mirror 613 and reflects a second portion of the light from an SLO 620 to the mirror 613, effectively combining vis-OCT and NIR SLO. The mirror 613 reflects the light to a GM 614 and into a fixation apparatus 630 that combines vis-OCT, NIR SLO and a visible fixation laser. The fixation laser, although visible, is detuned from the spectrum of the vis-OCT to prevent loss of the vis-OCT light.

The example SLO 620 includes an illumination path 2 and a collection path 3. Illumination path 2 consists of a light from a narrow band NIR source (e.g. super-luminescent diode (SLD) or diode laser). The CL 626 collimates illumination light in path 2, which passes through a polarizing beam splitter (PBS) 621 and then a linear polarizer 621. Light exiting the PBS 621 combines with the vis-OCT light at the DM1 612. A collection path 3 consists of the reflected light from the sample that reflects off the DM1 612. Light reflected from the DM1 612 reflects from the PBS 621 and goes through the linear polarizer 622 to a mirror M 624, which directs light through a CL 625 to the collecting channel (pin hole or multimode fiber). The intensity of the collected by a pin hole or fiber light can be detected by a detector (e.g. avalanche photodetector (APD) or photomultiplier tube (PMT)), for example.

The example fixation apparatus 630 takes light from the visible spectrum but is detuned from the OCT spectrum laser diode (for example LPS-675-FC) or target laser 638 and collimates the light with CL 636. Light from CL 636 impacts M 635 onto a MEMS 634. MEMS 634 scans a pre-programmed pattern onto DM2 (631), which combines the light from the fixation apparatus with the vis-OCT and SLO. The position of the pre-programmed pattern can be changed to guide the subject eye to different angles to enable imaging of different retina features (e.g. optic nerve head or macula for example).

Example BD-vis-OCT Processing

Signals from the example systems of FIGS. 1-6 can be used to process an ocular image or other image, for example. After ocular image acquisition, BD-vis-OCT can be performed using the fringes simultaneously captured by the pair of spectrometers 260-265, 390-395, 500. The fringes from the spectrometers 260-265, 390-395, 500 can be normalized by dividing each fringe by its respective mean spectrum. Fringes from the first spectrometer 260, 390, 560 can be resampled using an interpolation vector to match wavelength-dependent pixel elements of the first spectrometer 260, 390, 500 to wavelength-dependent pixel elements of the second spectrometer 265, 395, 565 with subpixel precision. The fringes from the second spectrometer 265, 395, 560 are then subtracted from the resampled fringes of the first spectrometer 260, 390, 565. Portions of the balanced fringes outside a region of spectral overlap are set equal to zero. Then SD-OCT image reconstruction is performed using k-space interpolation, automated dispersion compensation, and fast Fourier transformation (FFT), for example.

Example Interpolation Vector Selection

In certain examples, the pair of spectrometers 260-265, 390-395, 500 can include identical cameras having a one-dimensional (1D) array of N pixel elements (e.g., 256, 512, 1024, 2048, 4095, etc.). Although mostly overlapped through careful alignment, a wavelength distribution detected on the corresponding pixel elements of the spectrometers 260-265, 390-395, 500 are unique. Therefore, direct subtraction of simultaneously detected fringes in a BD-OCT system results in images with poor RIN suppression. This wavelength mismatch can be corrected by interpolating the wavelength-dependent fringes from one spectrometer 260, 390, 560 to match with the wavelength-dependent fringes from the other spectrometer 265, 395, 565 before subtraction. Thus, proper interpolation vector selection can achieve optimal or otherwise improved RIN suppression.

While a variety of approaches can be used to generate interpolation vectors, many such techniques suffer from strict pre-calibration or signal strength requirements that cannot always be met. For example, RIN-dominated images can be acquired, and a temporal correlation of the wavelength-dependent RIN is used to identify matching pixels between the two spectrometers. This technique uses a linear minimum squared error (LMMSE) estimation to obtain a transformation matrix, H, from a RIN-dominated dataset. Signals from spectrometers are defined as $\vec{n}_1$ and $\vec{n}_2$, respectively, with cross correlation matrix $R_{21}=\langle\vec{n}_2(\vec{n}_1)^T\rangle$ and autocorrelation matrices $R_{11}=\langle\vec{n}_1(\vec{n}_1)^T\rangle$ and $R_{22}=\langle\vec{n}_2(\vec{n}_2)^T\rangle$, where $\langle\ .\ .\ .\ \rangle$ denotes expectation. The LMMSE estimate is given by $H=R_{21}(R_{11})^{-1}$. A balanced signal is calculated by $S_{2\text{-}1}=S_2-HS_1$.

In another method, OCT images are used to match pixels that share highly-correlated noise and/or signal fluctuations. For example, noise-based cross-correlation (NCC) uses a RIN-dominated dataset to identify pixel pairs that share a highest temporal correlation. First, a cross-correlation matrix is generated consisting of Pearson's linear correlation coefficient for each pixel pair's temporal RIN profile. Next, pixel pairs sharing the maximum correlation are extracted. Lastly, an interpolation vector is generated by fitting a third order polynomial to the extracted pixel pairs. This vector is defined by:

$$L[n]=c_3[n]^3+c_2[n]^2+c_1[n]+c_0, \qquad \text{(Eq. 2)}$$

where, n is a pixel index, $c_0$ characterizes a bulk pixel offset between the two spectrometers, $c_1$ characterizes a pixel tilt, and $c_2$ and $c_3$ characterize non-linear pixel shifts introduced by spectrometer optics.

Image-based cross-correlation (ICC) is similar to NCC, but uses a scanned OCT image to identify wavelength-matched pixels. First, a cross-correlation matrix consisting of Pearson's linear correlation coefficient for each pixel pair's temporal signal profile is generated. The correlation matrix is then filtered by performing a two-dimensional (2D) Fast Fourier Transform (FFT) and applying a crossline mask to suppress artifacts from residual DC components. After inverse FFT, two points along the diagonal contour of the correlation matrix are manually selected and used to fit a first-order polynomial, which serves as the interpolation vector.

Example Adaptive Balance

Certain examples provide improved results to LMMSE, NCC, and ICC through adaptive balance, which iteratively updates an interpolation vector until RIN components concentrated near a DC term of a reconstructed OCT image are minimized or otherwise reduced. For example, the interpolation vector can be iteratively applied to one noise profile to align that noise profile with another noise profile. In Fourier-Domain OCT, for example, random (noise) and non-random components are considered in a single-depth profile before Fourier Transformation. The non-random component is a sum of an interference signal or fringe, that has an oscillation form resembling an Alternating Current (AC), and a non-alternating spectral shape of the source transformed after passing the optical system, which is called the "DC component". The DC component is removed before Fourier Transform to acquire the OCT signal.

RIN is a frequency-dependent noise that dominates at lower frequencies and falls off at higher frequencies. Thus, in OCT images, RIN manifests as a high background signal at lower depths that decays as depth increases. Adaptive balance uses this background information to iteratively change the interpolation vector coefficients until the high intensity background signal near the zero-delay (e.g., near the DC term) is minimized or otherwise reduced (e.g., iteratively apply the interpolation vector to a second noise profile to align the second noise profile with a first noise profile).

Figure 7:
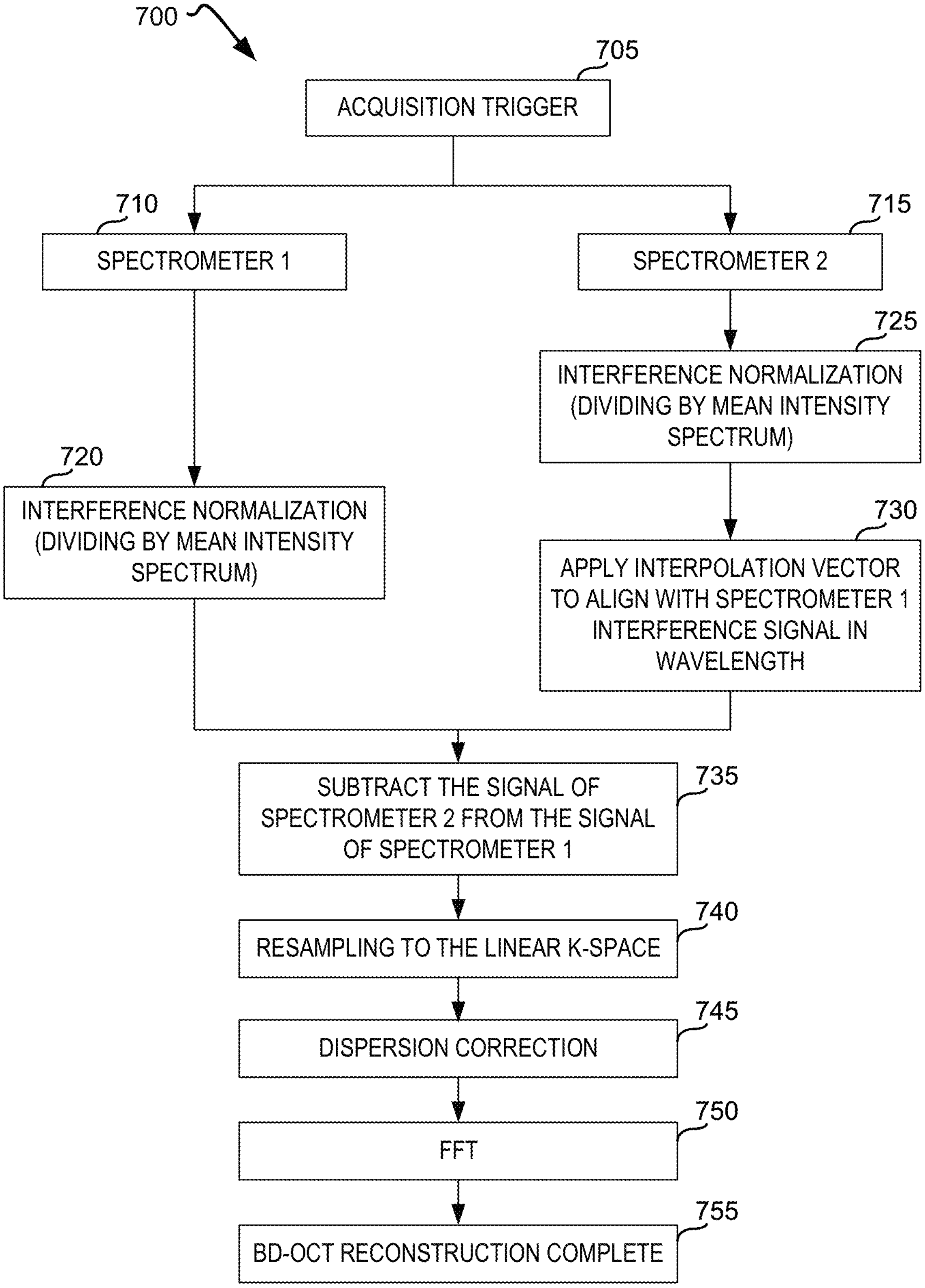
FIG. 7 is a flow diagram of an example method of image reconstruction using a dual spectrometer configuration.
Figure 8:
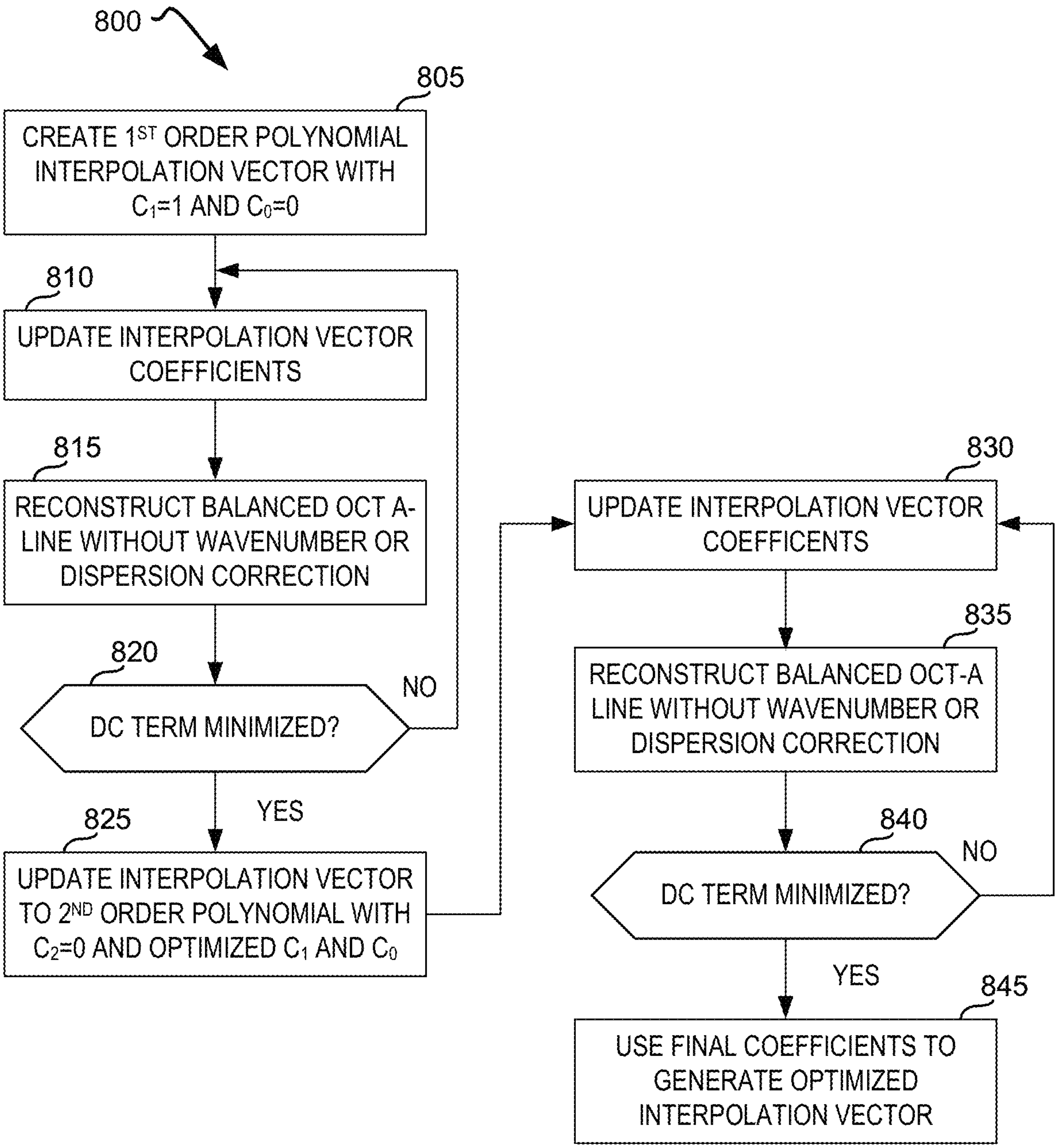
FIG. 8 is a flow diagram of an example adaptive balancing method using a dual spectrometer configuration.

Adaptive balancing is performed, as detailed in FIGS. 7-8, by initializing an interpolation vector with only first-order polynomial coefficients, where $[c_0, c_1]=[0,1]$. This interpolation vector is used to reconstruct a balanced A-line, $I_{bal}(z)$. Next, an optimization routine iteratively updates the interpolation vector coefficients $(c_0, c_1)$ until a mean value, $\bar{I}_{bal}(z)$, and variance near the zero-delay, up to a depth of $z_f$, are minimized or otherwise reduced using selected metrics. In certain examples, a penalty term, P, is included to help prevent unlikely coefficients from being generated by the optimizer, defined by:

$$P = \sum\nolimits_{n=0}^{n=N} \left| n - L[n] \right| + \sum\nolimits_{n=0}^{n=N} \begin{cases} 0, & 0 \leq L[n] \leq N \\ 1, & \text{otherwise} \end{cases}. \quad \text{(Eq. 3)}$$

This optimization process is described by:

$$\hat{C} = \underset{C}{\operatorname{argmin}} \left( \bar{I}_{bal}(z_f) + \operatorname{var}(I_{bal}(z_f)) + \alpha P \right), \quad \text{(Eq. 4)}$$

where Ć is an optimal or otherwise improved set of interpolation vector coefficients $[\hat{c}_0, \hat{c}_1]$, and α is a penalty term scaling factor.

Next, the optimization process described in Equation (3) is repeated after updating the interpolation vector to a second-order polynomial, where $[c_0, c_1, c_2]=[\hat{c}_0, \hat{c}_1, 0]$. After the function is minimized or otherwise reduced, the optimal interpolation vector coefficients $[\hat{c}_0, \hat{c}_1, \hat{c}_2]$ are used to generate a final interpolation vector. In many cases, the fitting order can be limited to the second order polynomial (e.g., $c_2$ is the highest order coefficient). However, higher order coefficients can be determined using similar approach until the level of the RIN suppression does not further improve.

Example Dual Spectrometry Methods

Flowcharts representative of example machine readable instructions, which may be executed by processor circuitry to operate the apparatus/systems described above with respect to FIGS. 1-6 are shown in FIGS. 7-8. The machine readable instructions may be one or more executable programs or portion(s) of an executable program for execution by processor circuitry, such as the processor circuitry 1412 shown in the example processor platform 1400 discussed below in connection with FIG. 14 and/or the example processor circuitry discussed below in connection with FIGS. 15 and/or 16. The program may be embodied in software stored on one or more non-transitory computer readable storage media such as a compact disk (CD), a floppy disk, a hard disk drive (HDD), a solid-state drive (SSD), a digital versatile disk (DVD), a Blu-ray disk, a volatile memory (e.g., Random Access Memory (RAM) of any type, etc.), or a non-volatile memory (e.g., electrically erasable programmable read-only memory (EEPROM), FLASH memory, an HDD, an SSD, etc.) associated with processor circuitry located in one or more hardware devices, but the entire program and/or parts thereof could alternatively be executed by one or more hardware devices other than the processor circuitry and/or embodied in firmware or dedicated hardware. The machine readable instructions may be distributed across multiple hardware devices and/or executed by two or more hardware devices (e.g., a server and a client hardware device). For example, the client hardware device may be implemented by an endpoint client hardware device (e.g., a hardware device associated with a user) or an intermediate client hardware device (e.g., a radio access network (RAN)) gateway that may facilitate communication between a server and an endpoint client hardware device). Similarly, the non-transitory computer readable storage media may include one or more mediums located in one or more hardware devices. Further, although the example program is described with reference to the flowcharts illustrated in FIGS. 7-8, many other methods of implementing the example apparatus described above may alternatively be used. For example, the order of execution of the blocks may be changed, and/or some of the blocks described may be changed, eliminated, or combined. Additionally or alternatively, any or all of the blocks may be implemented by one or more hardware circuits (e.g., processor circuitry, discrete and/or integrated analog and/or digital circuitry, an FPGA, an ASIC, a comparator, an operational-amplifier (op-amp), a logic circuit, etc.) structured to perform the corresponding operation without executing software or firmware. The processor circuitry may be distributed in different network locations and/or local to one or more hardware devices (e.g., a single-core processor (e.g., a single core central processor unit (CPU)), a multi-core processor (e.g., a multi-core CPU, an XPU, etc.) in a single machine, multiple processors distributed across multiple servers of a server rack, multiple processors distributed across one or more server racks, a CPU and/or a FPGA located in the same package (e.g., the same integrated circuit (IC) package or in two or more separate housings, etc.).

The machine readable instructions described herein may be stored in one or more of a compressed format, an encrypted format, a fragmented format, a compiled format, an executable format, a packaged format, etc. Machine readable instructions as described herein may be stored as data or a data structure (e.g., as portions of instructions, code, representations of code, etc.) that may be utilized to create, manufacture, and/or produce machine executable instructions. For example, the machine readable instructions may be fragmented and stored on one or more storage devices and/or computing devices (e.g., servers) located at the same or different locations of a network or collection of networks (e.g., in the cloud, in edge devices, etc.). The machine readable instructions may require one or more of installation, modification, adaptation, updating, combining, supplementing, configuring, decryption, decompression, unpacking, distribution, reassignment, compilation, etc., in order to make them directly readable, interpretable, and/or executable by a computing device and/or other machine. For example, the machine readable instructions may be stored in multiple parts, which are individually compressed, encrypted, and/or stored on separate computing devices, wherein the parts when decrypted, decompressed, and/or combined form a set of machine executable instructions that implement one or more operations that may together form a program such as that described herein.

In another example, the machine readable instructions may be stored in a state in which they may be read by processor circuitry, but require addition of a library (e.g., a dynamic link library (DLL)), a software development kit (SDK), an application programming interface (API), etc., in order to execute the machine readable instructions on a particular computing device or other device. In another example, the machine readable instructions may need to be configured (e.g., settings stored, data input, network addresses recorded, etc.) before the machine readable instructions and/or the corresponding program(s) can be executed in whole or in part. Thus, machine readable media, as used herein, may include machine readable instructions and/or program(s) regardless of the particular format or state of the machine readable instructions and/or program(s) when stored or otherwise at rest or in transit.

The machine readable instructions described herein can be represented by any past, present, or future instruction language, scripting language, programming language, etc. For example, the machine readable instructions may be represented using any of the following languages: C, C++, Java, C#, Perl, Python, JavaScript, HyperText Markup Language (HTML), Structured Query Language (SQL), Swift, etc.

As mentioned above, the example operations of FIGS. 7-8 may be implemented using executable instructions (e.g., computer and/or machine readable instructions) stored on one or more non-transitory computer and/or machine readable media such as optical storage devices, magnetic storage devices, an HDD, a flash memory, a read-only memory (ROM), a CD, a DVD, a cache, a RAM of any type, a register, and/or any other storage device or storage disk in which information is stored for any duration (e.g., for extended time periods, permanently, for brief instances, for temporarily buffering, and/or for caching of the information). As used herein, the terms non-transitory computer readable medium, non-transitory computer readable storage medium, non-transitory machine readable medium, and non-transitory machine readable storage medium are expressly defined to include any type of computer readable storage device and/or storage disk and to exclude propagating signals and to exclude transmission media. As used herein, the terms "computer readable storage device" and "machine readable storage device" are defined to include any physical (mechanical and/or electrical) structure to store information, but to exclude propagating signals and to exclude transmission media. Examples of computer readable storage devices and machine readable storage devices include random access memory of any type, read only memory of any type, solid state memory, flash memory, optical discs, magnetic disks, disk drives, and/or redundant array of independent disks (RAID) systems. As used herein, the term "device" refers to physical structure such as mechanical and/or electrical equipment, hardware, and/or circuitry that may or may not be configured by computer readable instructions, machine readable instructions, etc., and/or manufactured to execute computer readable instructions, machine readable instructions, etc.

The example systems described above can be used to execute a dual-spectrometer image reconstruction method, such as a method or process 700 described in connection with the example of FIG. 7. At block 705, a trigger begins acquisition of light. For example, a trigger from the processor 150, 270, 397 can activate the spectrometers 140, 260-265, 390-395, 500 to receive emitted/reflected/backscattered light from the sample arm 120, 220, 350 and the reference arm 130, 240, 355. At block 710, the first spectrometer 260, 390, 560 obtains light data, and, at block 715, the second spectrometer 265, 395, 565 obtains light data. For example, the spectrometers 140, 260-265, 390-395, 500 receive fringe patterns associated with light from the sample arm 120, 220, 350 and the reference arm 130, 240, 355.

At block 720, interference normalization is applied to the light received by the first spectrometer 260, 390, 560. For example, light received by the spectrometer 260, 390, 560 is divided by a mean intensity spectrum. More specifically, the received light can be normalized by dividing the fringe by its respective mean spectrum.

At block 725, interference normalization is applied to the light received by the second spectrometer 265, 395, 565. For example, light received by the spectrometer 265, 395, 565 is divided by a mean intensity spectrum. More specifically, the received light can be normalized by dividing the fringe by its respective mean spectrum.

At block 730, an interpolation vector is applied to the normalized fringe of the second spectrometer 265, 395, 565 to align the light fringe with the normalized light fringe of the first spectrometer 260, 290, 560. For example, an interpolation vector or transformation matrix is applied to interpolate pixels from the second spectrometer 265, 395, 565 to the first spectrometer 260, 390, 560. Interpolation vector selection from a spectrometer pair can be performed using either a RIN- or signal-dominated dataset, for example.

At block 735, a signal of the second spectrometer 265, 395, 565 is subtracted from a signal of the first spectrometer 260, 390, 560. For example, subtracting an interferogram signal of the second spectrometer 265, 395, 565 from an interferogram signal of the first spectrometer 250, 390, 560 results in a summing or addition of x-shifted interference signals while suppressing RIN.

At block 740, light image data is resampled to a linear k-space. For example, light fringe data from the first and second spectrometers 260-265, 390-395, 560-565 is interpolated by resampling the data to be linear and equidistant in k-space. At block 745, dispersion correction is applied to the resampled data. For example, dispersion of light on the fringe is corrected or compensated. At block 750, the corrected, equidistant in frequency light image data is then processed using a Fast Fourier Transform (FFT). The FFT filters to further suppress RIN and/or other noise in the image data. At block 755, image reconstruction is complete. The image can then be output, saved, analyzed, etc., to drive patient diagnosis and treatment, for example. As such, adaptive balance is applied to generate an interpolation vector to optimize and/or otherwise improve RIN and/or other noise reduction in an ocular OCT image. Such a process can be iterative, for example, until noise profiles from different spectrometers are aligned.

FIG. 8 is a flow diagram of an example adaptive balancing method or process 800. The example process 800 of FIG. 8 uses a dual spectrometer configuration and achieves interpolation vector optimization using a second order polynomial fit. Higher order polynomial fit can be achieved similarly by calculating C3, C4, . . . . CN coefficients, where the N is the highest order of the fit.

As shown in the example of FIG. 8 an interpolation vector is generated and optimized or otherwise improved. The interpolation vector can be applied to the normalized fringe of the second spectrometer 265, 395, 565 to align the light fringe (e.g., a noise profile) with the normalized light fringe (e.g., another noise profile) of the first spectrometer 260, 290, 560, for example (such as at block 730 above).

At block 805, an interpolation vector is created or otherwise initialized with first-order polynomial coefficients, $C_1=1$ and $C_0=0$. At block 810, the coefficients of the interpolation vector are updated. For example, an optimization routine or process (e.g., reflected in Equation 4) updates the coefficients of the interpolation vector. In certain examples, a penalty term, P, can be included to help prevent unlikely coefficients from being generated by the optimizer. Example use of the penalty term is illustrated in the example of Equation 3.

At block 815, a balanced OCT A-line is reconstructed using the interpolation vector. For example, the interpolation vector is used to reconstruct a balanced A-line, $I_{bal}(z)$., without wave number or dispersion correction (DPC). The A-line is a 1D OCT image along an axial line (an A-line). The A-line represents a time involved to detect pulses of light reflected from sub-surfaces within ocular tissue, for example.

At block 820, a direct current (DC) component of the reconstructed signal (DC term) is evaluated to determine whether it has been minimized or otherwise reduced to a given level or threshold. The DC term can be represented, for example, by a mean value, $\bar{I}_{bal}(z)$, and a variance near the zero-delay, up to a depth of $z_f$. If the DC term has not been minimized or sufficiently reduced, then control reverts to block 810 to update interpolation vector coefficients. If the DC has been minimized or sufficiently reduced to the given level, then control proceeds to block 825. For example, an optimization routine or process (e.g., reflected in Equation 4) updates the coefficients until the mean value, $\bar{I}_{bal}(z)$, and variance near the zero-delay, up to a depth of $z_f$, are minimized or otherwise reduced. In certain examples, a penalty term, P, can be included to help prevent unlikely coefficients from being generated by the optimizer. Example use of the penalty term is illustrated in the example of Equation 3.

At block 825, the interpolation vector is updated to a second-order polynomial with $C_2=0$ and optimized. At block 830, the interpolation vector coefficients are updated. For example, the optimization process described in Equation 4 can be repeated after updating the interpolation vector to a second-order polynomial, where $[c_0, c_1, c_2]=[\hat{c}_0, \hat{c}_1, 0]$. At block 835, a balanced OCT A-line is reconstructed using the interpolation vector. For example, the interpolation vector is used to reconstruct a balanced A-line, $I_{bal}(z)$., without wave number or dispersion correction.

At block 840, the DC term is again evaluated to determine whether the term has been minimized or otherwise reduced to a specified level or threshold. If not, then the process reverts to block 830 to iteratively update interpolation vector coefficients. If the DC has been minimized or sufficiently reduced, then, at block 845, the optimal interpolation vector coefficients $[\hat{c}_0, \hat{c}_1, \hat{c}_2]$ are used to generate the final interpolation vector. The final interpolation vector can then be used to align the output of the second spectrometer with the output of the first spectrometer (e.g., block 730 of the example of FIG. 7).

A variety of image quality metrics can be used to compare BD-vis-OCT images. In certain examples, a standard deviation of the noise floor, $\sigma_{floor}$, can be calculated to quantify a remaining pixel uncertainty after RIN suppression. Noise floor standard deviation can be recorded between the zero-delay position and the surface of the eye being imaged. A peak signal-to-noise ratio (PSNR) can be calculated to quantify the pixel uncertainty with respect to a maximum signal value. In certain examples, PSNR can be defined as:

$$PSNR = 20\ \log_{10}(A_{sig}/\sigma_{floor}), \tag{Eq. 5}$$

where $A_{sig}$ is a maximum intensity value within a region of interest.

A contrast-to-noise ratio (CNR) can be measured to quantify image contrast with respect to pixel uncertainty. CNR is defined as $$CNR = 10\log_{10}\left((A_{sig} - A_{floor})/\sqrt{\sigma_{sig}^2 + \sigma_{floor}^2}\right), \tag{Eq. 6}$$

where $A_{floor}$ is a mean intensity of the noise floor, and $\sigma_{sig}$ is a standard deviation of the signal region. For cases in which the noise floor is greater than the signal, resulting in a complex CNR, the signal is considered noise-floor-limited (NFL). CNR can be evaluated at various layers of the eye to identify depth dependent changes in image quality, for example.

As such, adaptive balancing can calibrate or align a first photodetector with a second photodetector (e.g., align the second spectrometer 265, 395, 565 with the first spectrometer 260, 290, 560, etc.). For example noise profiles can be aligned (e.g., iteratively) to adaptively calibrate the photodetectors. The image used to measure and compare the noise profile can be acquired from a human eye, an artificial sample, etc. Canceling of noise between the photodetectors can be performed each time before a human eye is imaged, at other times when an image is not being obtained, etc. The apparatus can thus be calibrated for ocular image acquisition and processing without requiring a separate, repeated calibration action. Instead, noise canceling through adaptive balancing can be incorporated into normal operation for image acquisition.

Example Results

An optical intensity detected by the spectrometers 140, 260-265, 390-395, 500 has a squared relationship with RIN.

As such, adjusting a camera gain of the spectrometers 140, 260-265, 390-395, 500 to vary the values of the detected optical intensity without saturation varies the RIN level in the light image data.

Figure 9A:
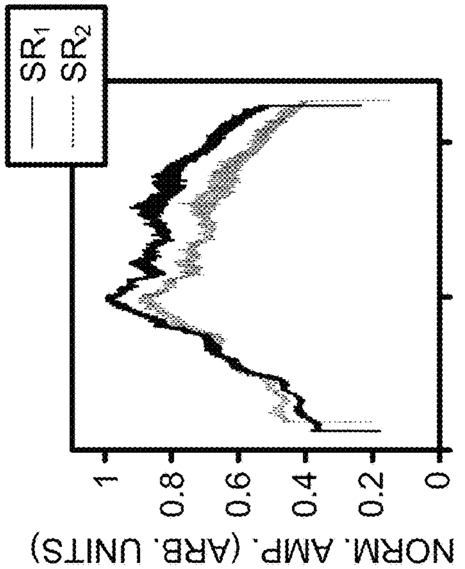
FIG. 9A shows example measurements obtained using apparatus and methods disclosed and described herein, such as the apparatus of FIGS. 1-6 and the methods of FIGS. 7-8.
Figure 9B:
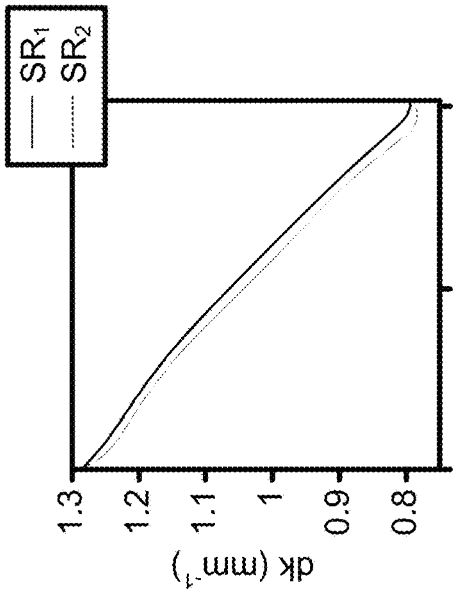
FIG. 9B shows example measurements obtained using apparatus and methods disclosed and described herein, such as the apparatus of FIGS. 1-6 and the methods of FIGS. 7-8.
Figure 9C:
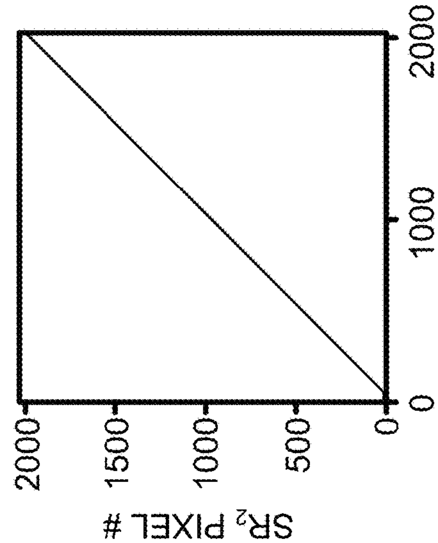
FIG. 9C shows example measurements obtained using apparatus and methods disclosed and described herein, such as the apparatus of FIGS. 1-6 and the methods of FIGS. 7-8.
Figure 9D:
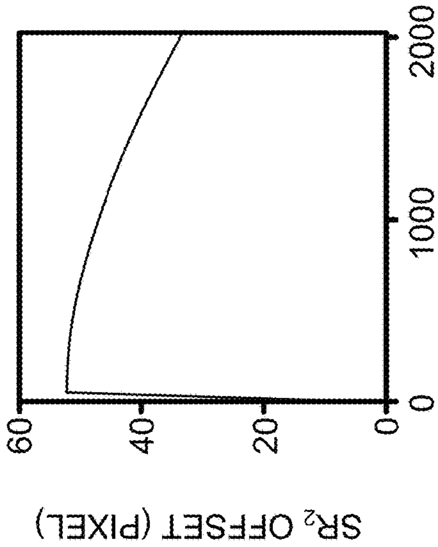
FIG. 9D shows example measurements obtained using apparatus and methods disclosed and described herein, such as the apparatus of FIGS. 1-6 and the methods of FIGS. 7-8.

FIGS. 9A-9D show example values of pixel data from the first spectrometer $SR_1$ 260, 390 and the second spectrometer $SR_2$ 265, 395. FIG. 9A depicts example reference arm spectra detected by $SR_1$ (solid line) and $SR_2$ (dashed line). FIG. 9B shows example k-spacing of $SR_1$ (solid line) and $SR_2$ (dashed line). FIG. 9C shows an example pixel map from $SR_2$ to $SR_1$. FIG. 9D shows an example $SR_2$ pixel offset with respect to $SR_1$ pixel number.

Figure 10A:
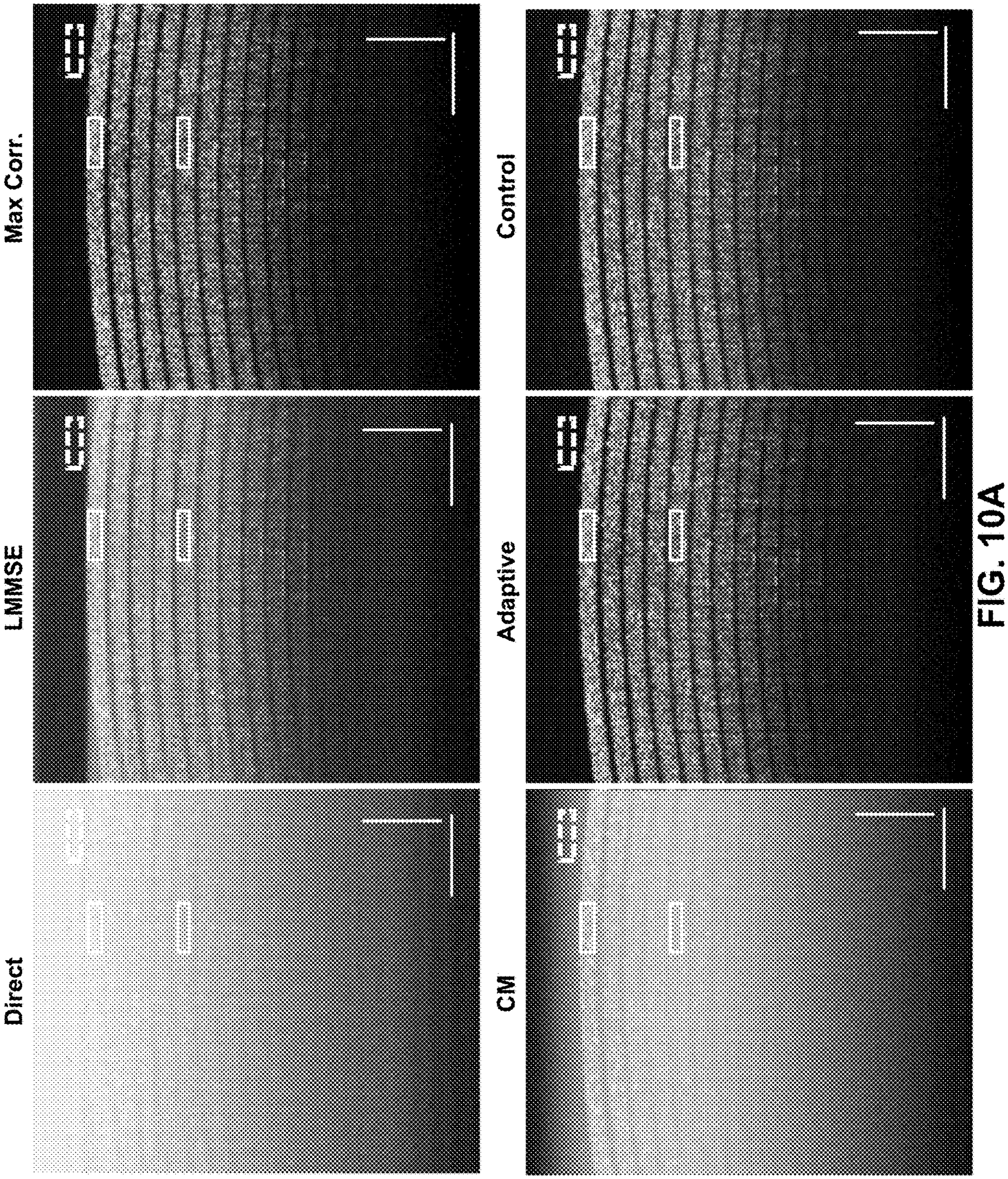
FIG. 10A shows a set of example images obtained using apparatus and methods disclosed and described herein, such as the apparatus of FIGS. 1-6 and the methods of FIGS. 7-8.
Figure 10B:
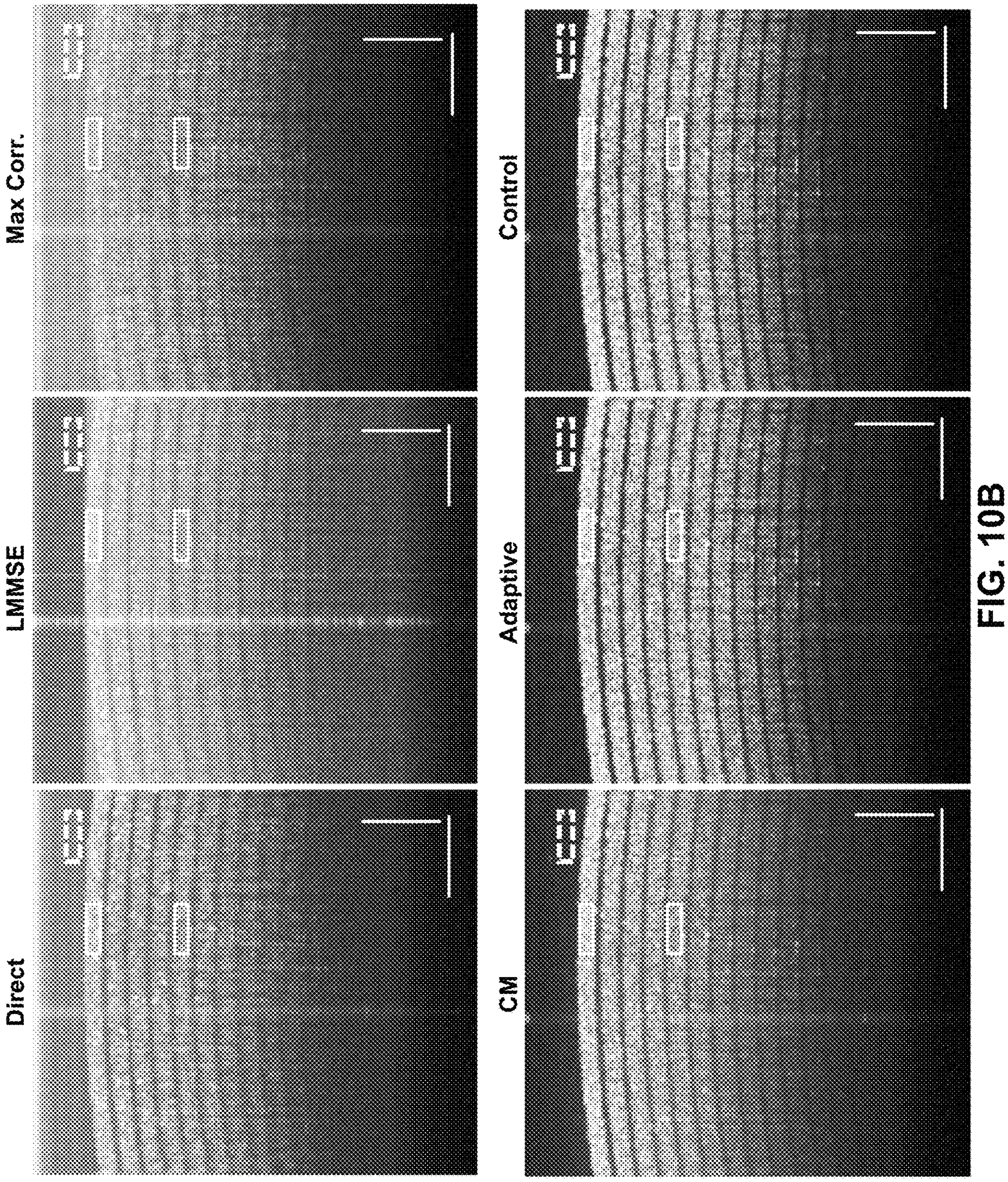
FIG. 10B shows a set of example images obtained using apparatus and methods disclosed and described herein, such as the apparatus of FIGS. 1-6 and the methods of FIGS. 7-8.
Figure 10C:
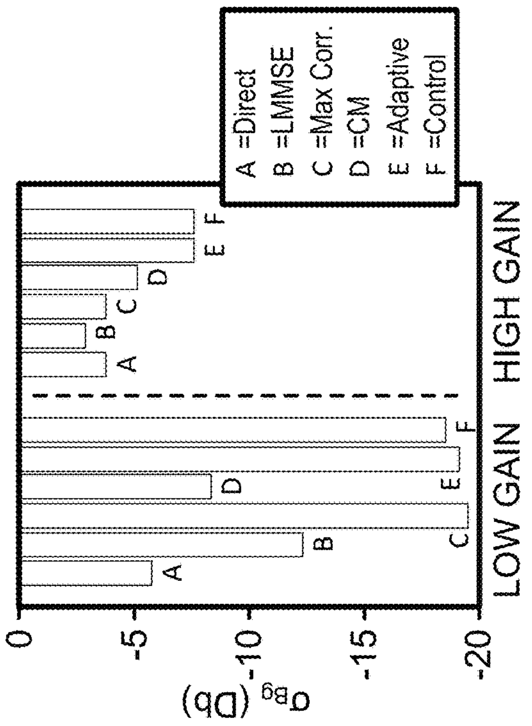
FIG. 10C shows example measurements obtained using apparatus and methods disclosed and described herein, such as the apparatus of FIGS. 1-6 and the methods of FIGS. 7-8.
Figure 10D:
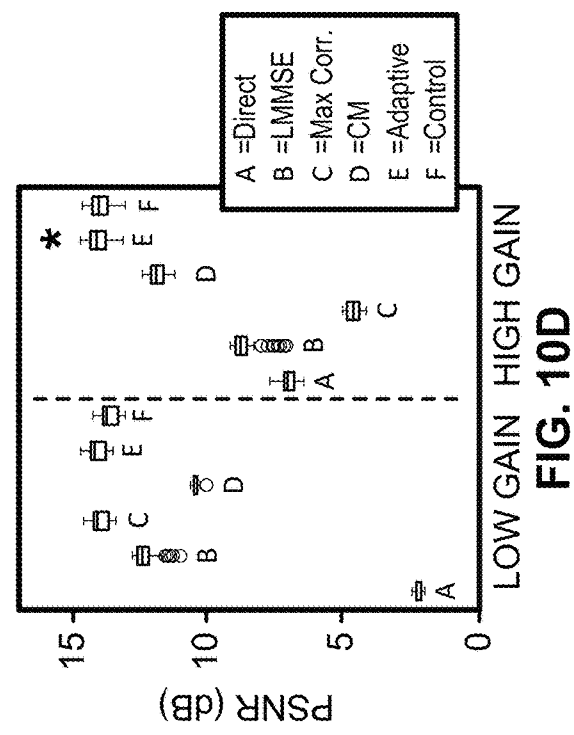
FIG. 10D shows example measurements obtained using apparatus and methods disclosed and described herein, such as the apparatus of FIGS. 1-6 and the methods of FIGS. 7-8.
Figure 10E:
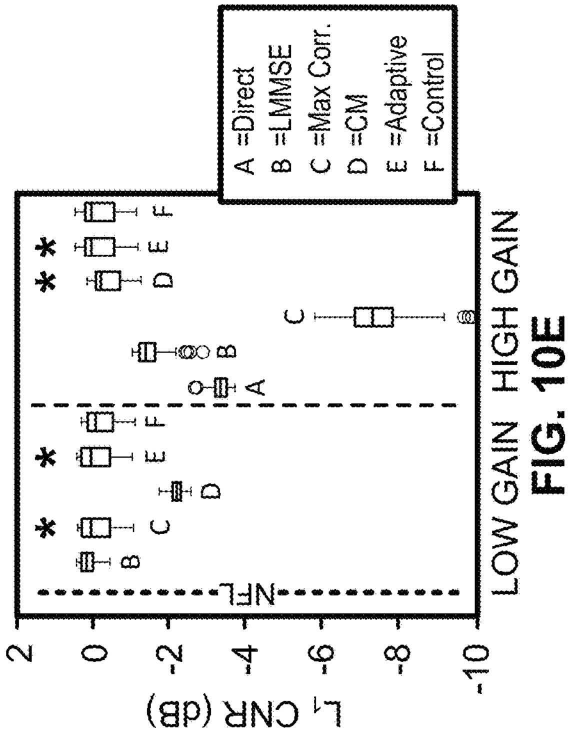
FIG. 10E shows example measurements obtained using apparatus and methods disclosed and described herein, such as the apparatus of FIGS. 1-6 and the methods of FIGS. 7-8.
Figure 10F:
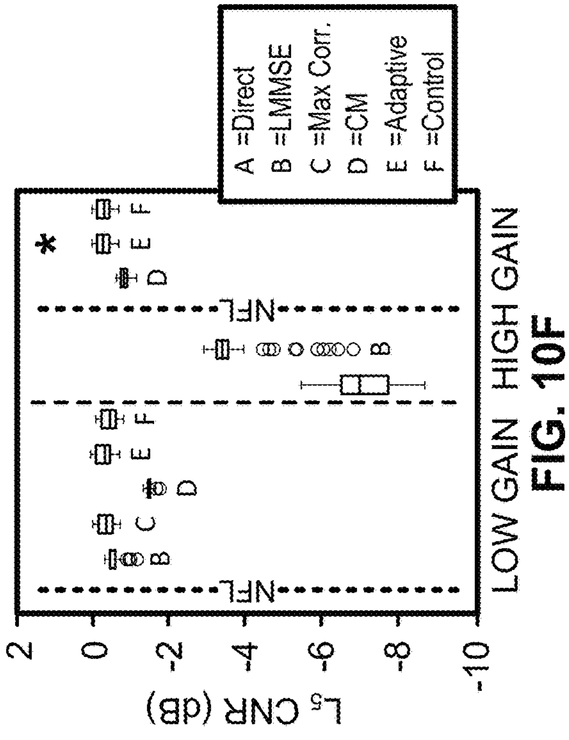
FIG. 10F shows example measurements obtained using apparatus and methods disclosed and described herein, such as the apparatus of FIGS. 1-6 and the methods of FIGS. 7-8.

FIGS. 10A-10B illustrate example acquisition images. Phantom images shown were acquired before and after increasing camera gain by a factor of 16. The images were then used as input datasets for generating interpolation vectors using the methods described above. FIG. 10A shows balanced B-scan images with low camera gain after subpixel matching using (from left to right in FIG. 10A) direct (1:1) matching, LMMSE, NCC (represented in the figures as maximum correlation or "Max Corr." because, as described above, NCC uses a RIN-dominated dataset to identify pixel pairs that share a highest temporal correlation (Max Corr.)), ICC (represented in the figures as "CM" because, as described above, ICC uses a cross-correlation matrix (CM) consisting of Pearson's linear correlation coefficient for each pixel pair's temporal signal profile), adaptive balance, and a pre-calibrated control method. Qualitatively, lower SNR was observed for direct and ICC methods compared to the NCC, adaptive balance, and control methods. In contrast, FIG. 10B shows phantom images with high camera gain after pixel matching using (from left to right in FIG. 10B) direct matching, LMMSE, NCC, ICC, adaptive balance, and the pre-calibrated control method. Comparatively, the direct, LMMSE, and NCC methods all show lower SNR than the ICC, adaptive, and control matching methods with high camera gain.

Next, image quality metrics are compared for each pixel-matching method and camera gain level. Example plots in FIGS. 10C-10F respectively depict the Øfloor, PSNR, layer 1 ($L_1$) CNR, and layer 5 ($L_5$) CNR for each mapping method and camera gain level. The (*) in FIGS. 10C-10F indicates no significant difference with respect to the control results. For low camera gain, both the NCC and adaptive balance methods consistently outperformed the control method with decreased $\sigma_{floor}$, increased PSNR and $L_5$ CNR, and comparable $L_1$ CNR. LMMSE produced an increased $L_1$ CNR value compared to the control method but performed worse across all other metrics. Conversely, direct mapping and ICC methods all performed consistently worse than the control method with low amplification. For high camera gain, only the adaptive balance method showed comparable image quality to the pre-calibrated control method for $\sigma_{floor}$, PSNR, $L_1$CNR, and $L_5$ CNR.

Figure 11A:
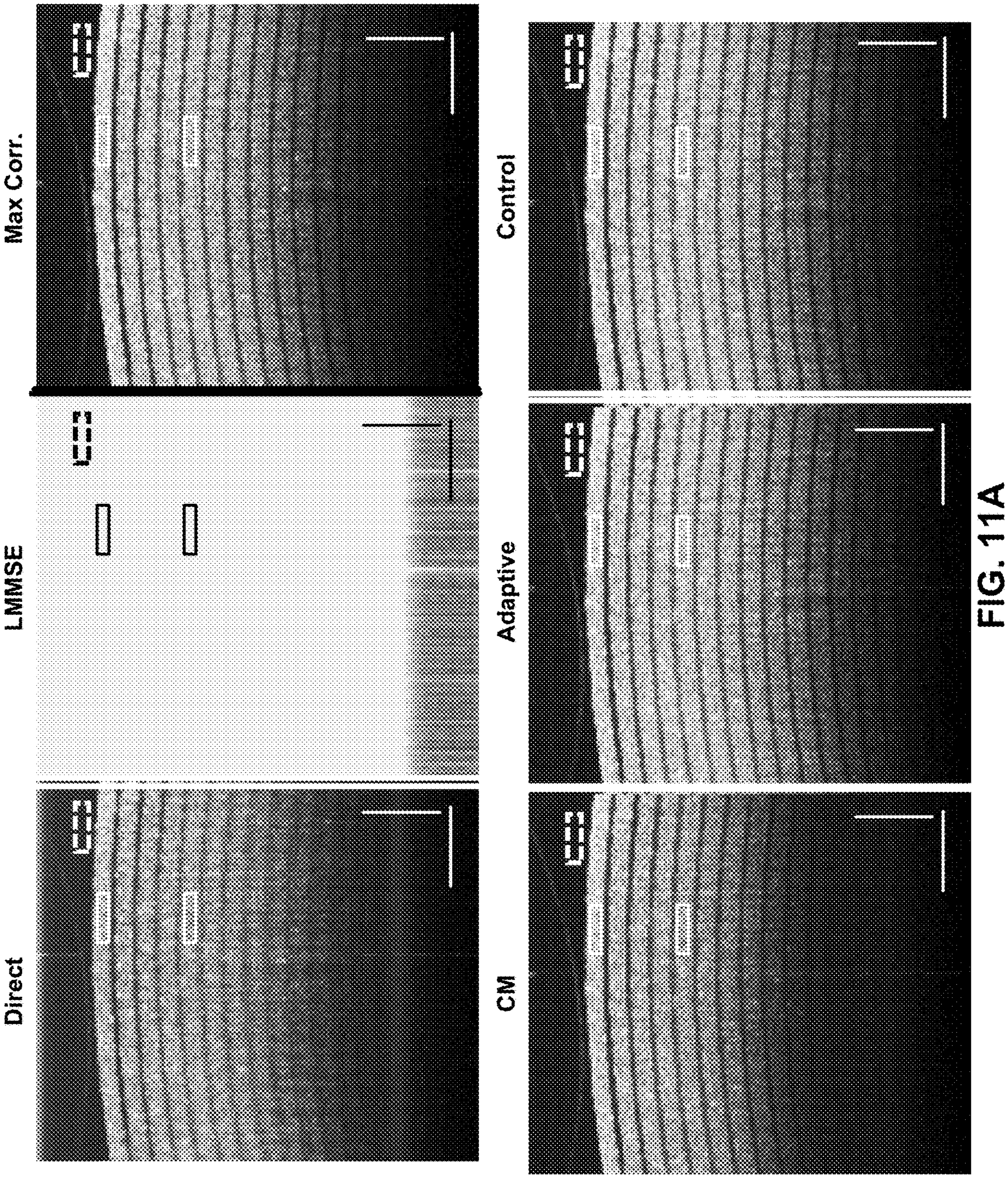
FIG. 11A shows a set of example images obtained using apparatus and methods disclosed and described herein, such as the apparatus of FIGS. 1-6 and the methods of FIGS. 7-8.

Pixel-matching methods can also be compared based on short (e.g., 8 μs) and long (e.g., 40 μs) spectrometer camera exposure time values. FIG. 11A shows resulting phantom B-scan images for shorter exposure time after applying (from left to right in FIG. 11A) direct matching, LMMSE, NCC, ICC, adaptive balance, and pre-calibrated control matching methods.

Figure 11B:
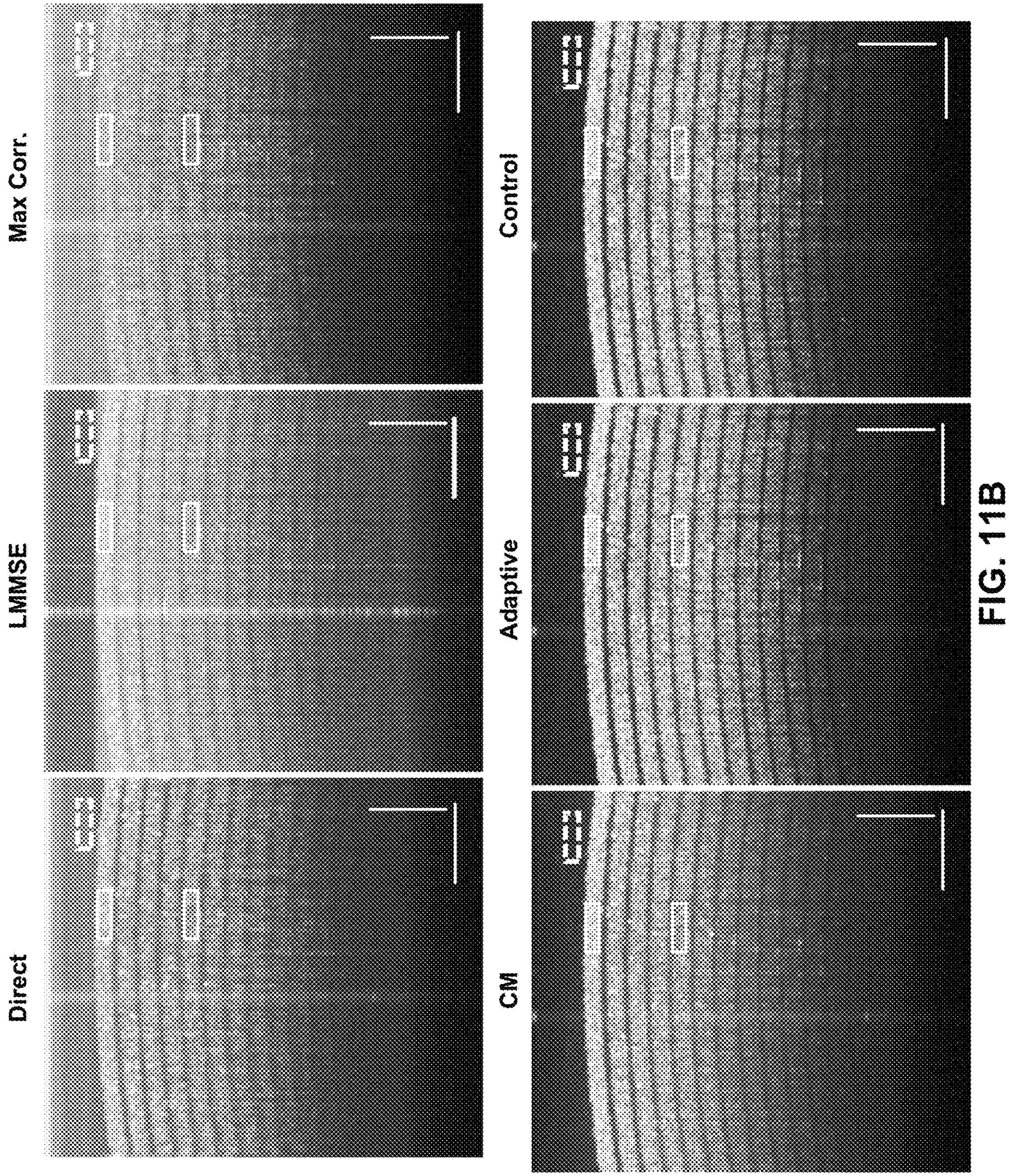
FIG. 11B shows a set of example images obtained using apparatus and methods disclosed and described herein, such as the apparatus of FIGS. 1-6 and the methods of FIGS. 7-8.
Figure 11C:
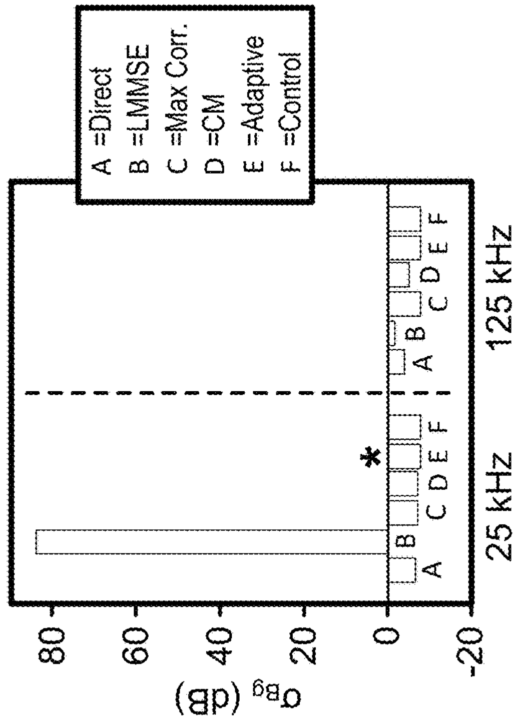
FIG. 11C shows example measurements obtained using apparatus and methods disclosed and described herein, such as the apparatus of FIGS. 1-6 and the methods of FIGS. 7-8.
Figure 11D:
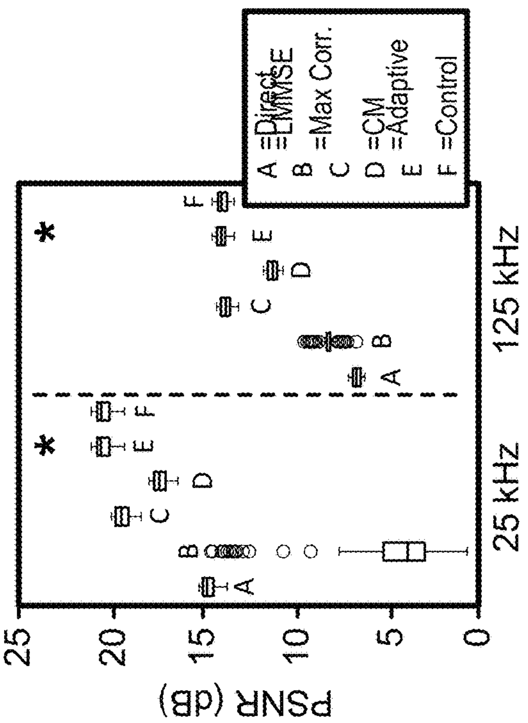
FIG. 11D shows example measurements obtained using apparatus and methods disclosed and described herein, such as the apparatus of FIGS. 1-6 and the methods of FIGS. 7-8.
Figure 11E:
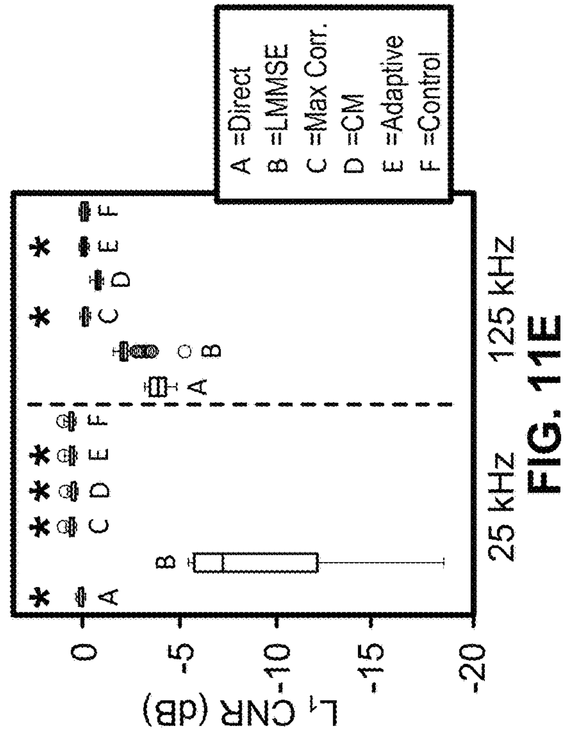
FIG. 11E shows example measurements obtained using apparatus and methods disclosed and described herein, such as the apparatus of FIGS. 1-6 and the methods of FIGS. 7-8.
Figure 11F:
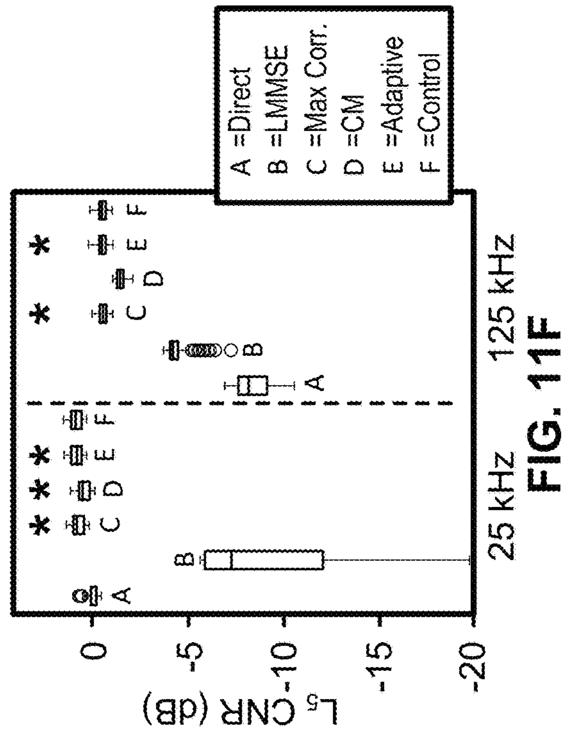
FIG. 11F shows example measurements obtained using apparatus and methods disclosed and described herein, such as the apparatus of FIGS. 1-6 and the methods of FIGS. 7-8.

Qualitatively, reduced SNR is observed from the LMMSE and ICC methods compared to the control image. SNR appeared to be comparable to the control for direct, NCC, and adaptive methods; however, the sharpness of the layers reduces with depth for the direct matching method. FIG. 11B shows phantom B-scan images for longer exposure time after applying (from left to right in FIG. 11B) direct matching, LMMSE, NCC, ICC, adaptive balance, and pre-calibrated control methods. SNR appeared to be lower for the direct, LMMSE, and ICC methods and more comparable to the control for the NCC and adaptive balance methods.

Example quantitative image quality metrics are shown in FIGS. 11C-11F, including $\sigma_{floor}$, PSNR, $L_1$ CNR, and $L_5$ CNR. For short spectrometer camera exposure time, adaptive balance had comparable image quality to the control case for all four metrics. NCC and ICC methods had comparable image quality to the control method for $L_1$ and $L_5$ CNR and direct matching had comparable quality for $L_1$ CNR. For long spectrometer camera exposure time, adaptive balance performed as well as the pre-calibrated control method for all metrics other than $\sigma_{floor}$. NCC showed comparable performance for $L_1$ and $L_5$ CNR.

Figure 12A:
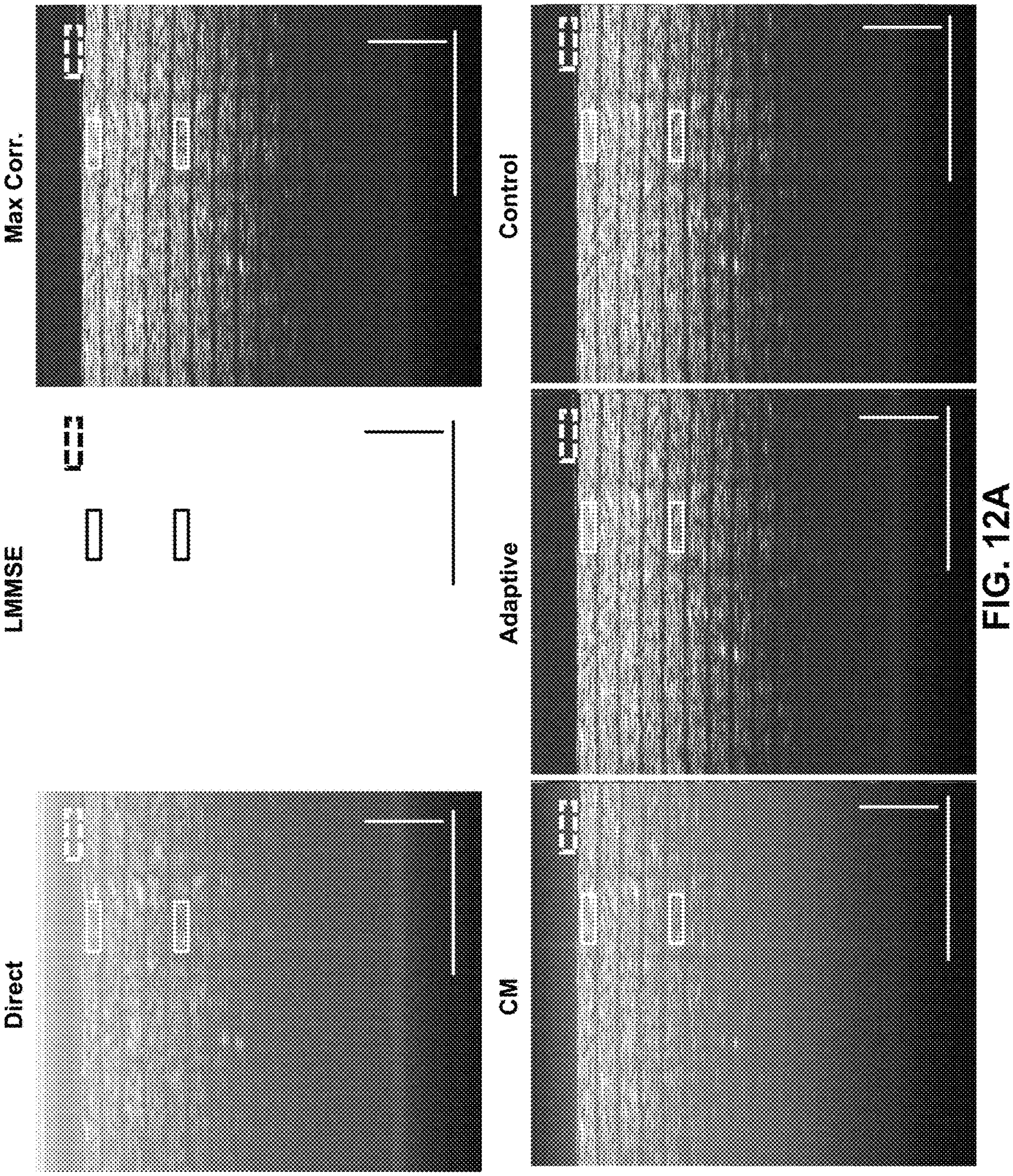
FIG. 12A shows a set of example images obtained using apparatus and methods disclosed and described herein, such as the apparatus of FIGS. 1-6 and the methods of FIGS. 7-8.
Figure 12B:
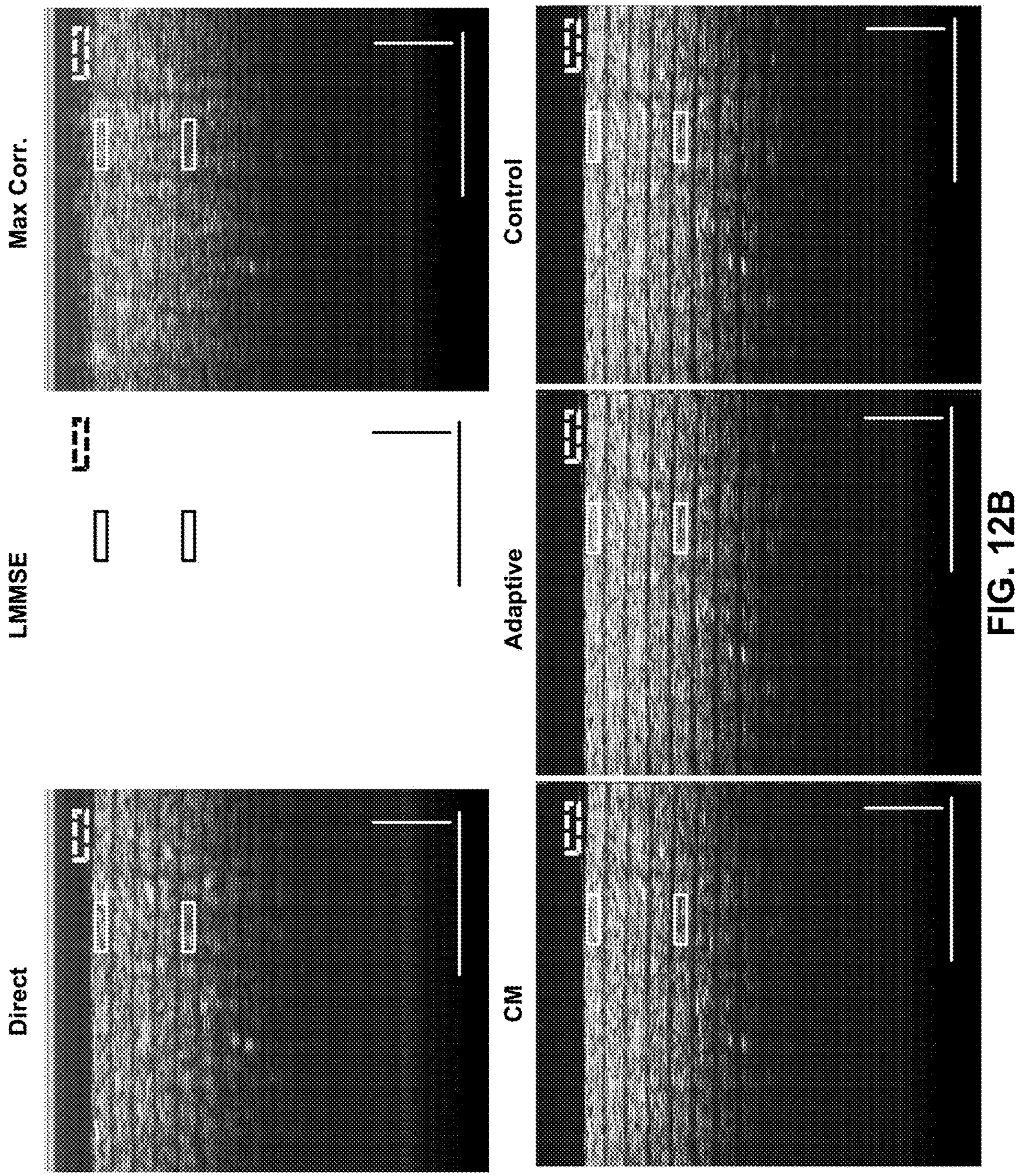
FIG. 12B shows a set of example images obtained using apparatus and methods disclosed and described herein, such as the apparatus of FIGS. 1-6 and the methods of FIGS. 7-8.
Figure 12C:
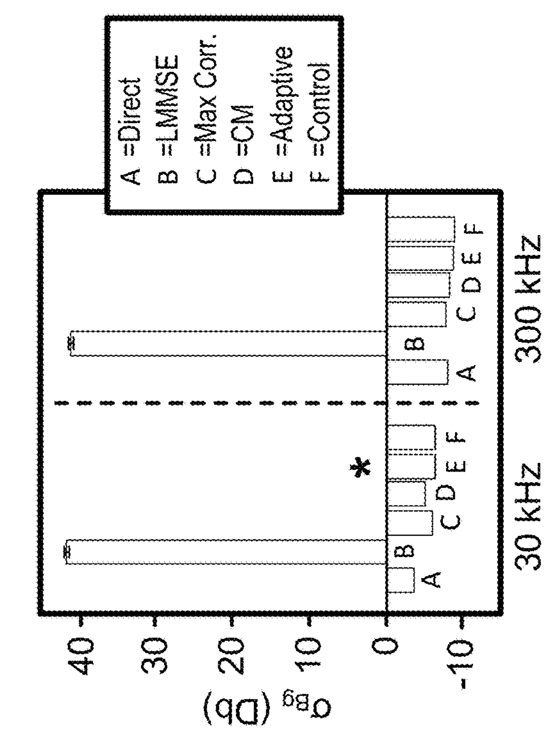
FIG. 12C shows example measurements obtained using apparatus and methods disclosed and described herein, such as the apparatus of FIGS. 1-6 and the methods of FIGS. 7-8.
Figure 12D:
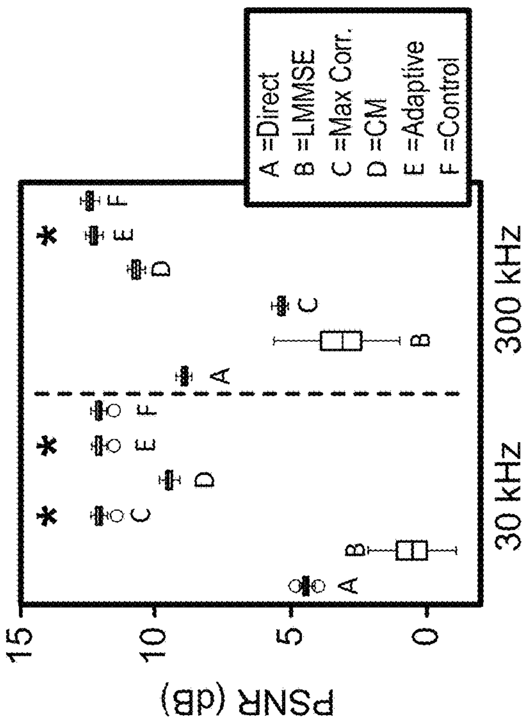
FIG. 12D shows example measurements obtained using apparatus and methods disclosed and described herein, such as the apparatus of FIGS. 1-6 and the methods of FIGS. 7-8.
Figure 12E:
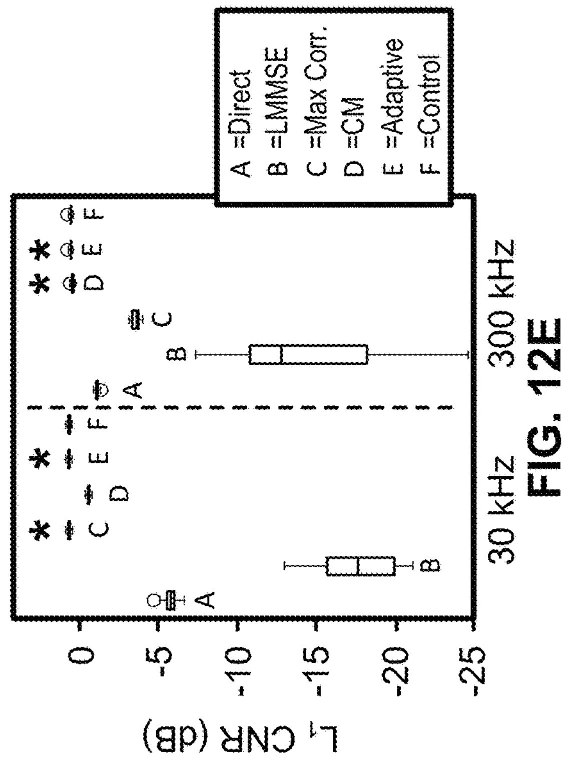
FIG. 12E shows example measurements obtained using apparatus and methods disclosed and described herein, such as the apparatus of FIGS. 1-6 and the methods of FIGS. 7-8.
Figure 12F:
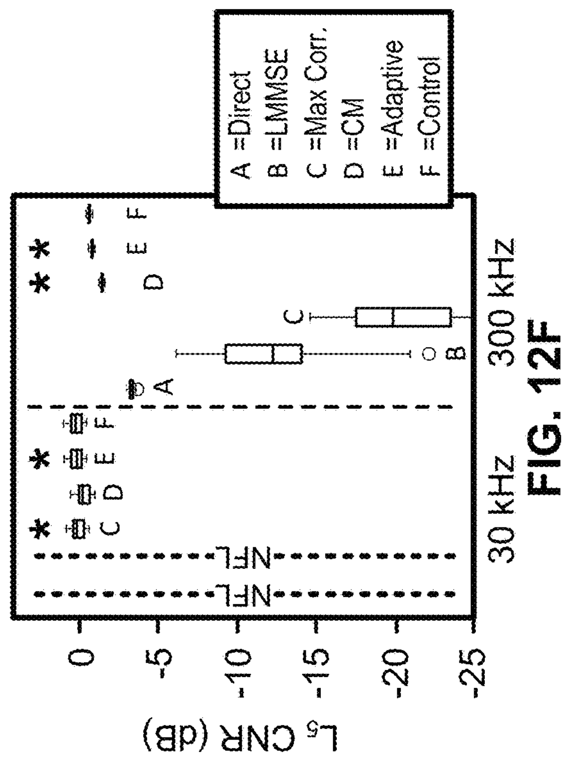
FIG. 12F shows example measurements obtained using apparatus and methods disclosed and described herein, such as the apparatus of FIGS. 1-6 and the methods of FIGS. 7-8.

Additionally, performance of each spectrometer matching method can be compared with low (30 MHz) and high (300 MHz) SC laser repetition rates. FIG. 12A shows the tape phantom B-scan acquired using the low repletion rate with (from left to right in FIG. 12A) direct matching, LMMSE, NCC, ICC, adaptive balance, and pre-calibrated control methods. Qualitatively, low SNR images were observed after applying direct matching, LMMSE, and ICC methods. SNR was comparable to the control method for NCC and adaptive balance methods. FIG. 12B shows the phantom B-scans acquired using the high repetition rate after applying (from left to right in FIG. 12B) direct matching, LMMSE, NCC, ICC, adaptive balance, and pre-calibrated control methods. SNR appeared to be reduced after applying direct matching, LMMSE, and NCC matching methods. SNR was comparable to the control method for ICC and adaptive balance methods.

Comparisons of the image quality metrics are shown in FIGS. 12C-12F for $\sigma_{floor}$, PSNR, $L_1$ CNR, and $L_5$ CNR, respectively, where (*) indicates no statistically significant difference with respect to the control result. For a low repetition rate, the NCC and adaptive balance showed comparable performance to the control method for all image quality metrics. For a high repetition rate, adaptive balance had comparable performance to the control method for all image quality metrics. The ICC method also had $L_1$ and $L_5$ CNR values comparable to the control method.

To further demonstrate the performance of adaptive balance, a human retina image is used as input to determine a spectrometer interpolation vector. Human imaging is performed using the BD-vis-OCT system described above.

Figure 13A:
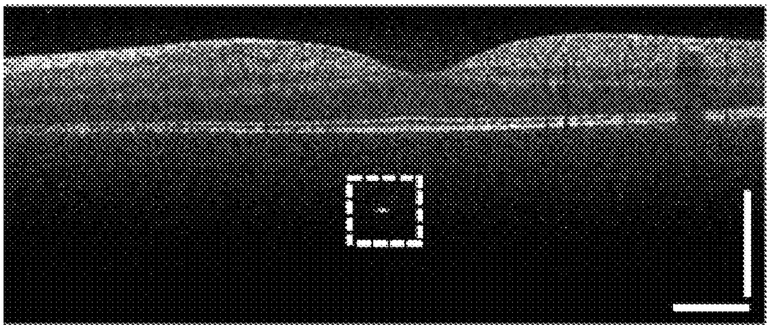
FIG. 13A shows an example image obtained using apparatus and methods disclosed and described herein, such as the apparatus of FIGS. 1-6 and the methods of FIGS. 7-8.
Figure 13D:
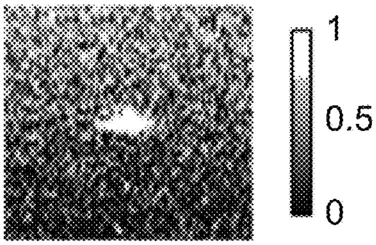
FIG. 13D shows an example image obtained using apparatus and methods disclosed and described herein, such as the apparatus of FIGS. 1-6 and the methods of FIGS. 7-8.
Figure 13B:
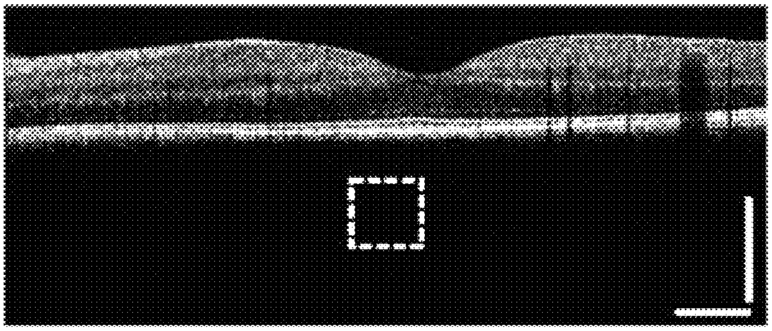
FIG. 13B shows an example image obtained using apparatus and methods disclosed and described herein, such as the apparatus of FIGS. 1-6 and the methods of FIGS. 7-8.
Figure 13E:
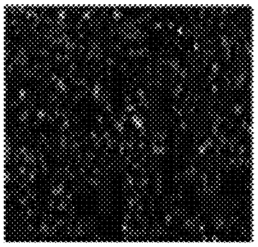
FIG. 13E shows an example image obtained using apparatus and methods disclosed and described herein, such as the apparatus of FIGS. 1-6 and the methods of FIGS. 7-8.
Figure 13C:
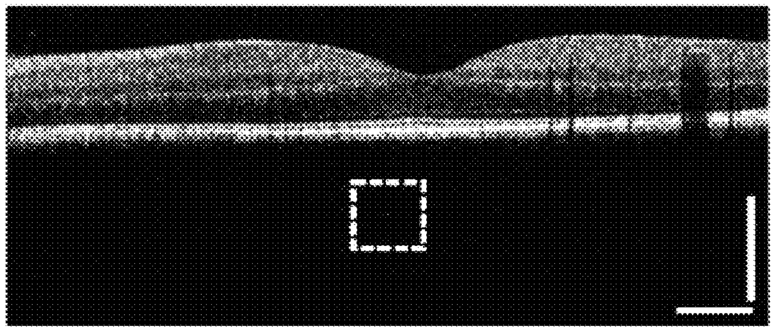
FIG. 13C shows an example image obtained using apparatus and methods disclosed and described herein, such as the apparatus of FIGS. 1-6 and the methods of FIGS. 7-8.
Figure 13F:
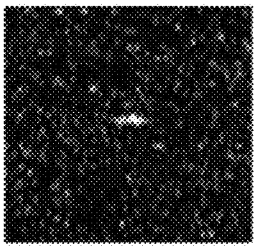
FIG. 13F shows an example image obtained using apparatus and methods disclosed and described herein, such as the apparatus of FIGS. 1-6 and the methods of FIGS. 7-8.

FIGS. 13A-13C respectively show an example retinal B-scan image after applying direct matching (FIG. 13A), adaptive balance (FIG. 13B), and a pre-calibrated control interpolation vector (FIG. 13C). Qualitatively, the adaptive and pre-calibrated control methods show the least amount of background noise and higher SNR compared to direct matching. Further, the adaptive balance method shows better autocorrelation artifact removal, as indicated by the white boxes in FIGS. 13A-13C, compared to the direct matching and pre-calibrated control methods. The magnified and contrast-adjusted images in FIGS. 13D-13F expand on the regions highlighted in FIGS. 13A-13 C to further compare the level of RIN and autocorrelation artifact removal using direct matching, adaptive balance, and control, respectively.

Thus, certain examples provide an adaptive, calibration-free method and associated system to match wavelength-dependent pixel elements of a spectrometer pair with sub-pixel accuracy, referred to herein as adaptive balance. The robustness of this method is demonstrated against other subpixel matching techniques by comparing each method's ability to suppress RIN from phantom and human retinal images acquired with varying spectrometer camera gain, exposure time, and SC laser repetition rate.

RIN is a frequency-dependent noise that is strongest at lower frequencies and falls off rapidly at higher frequencies. Thus, in traditional SD-OCT images, RIN manifests as a high-intensity background signal near the zero-delay position that falls off as depth increases. The RIN bandwidth, or depth at which the background intensity reaches 6 dB of its zero-delay intensity, is inversely proportional to spectrometer's exposure time and SC laser's repetition rate. Thus, the RIN bandwidth reduces with increased spectrometer camera exposure time and SC laser repetition rate. However, prolonged spectrometer exposure time leads to reduced A-line rate, which increases the probability of motion artifacts in human imaging. In addition, SC lasers with high repetition rates are significantly more expensive, which can be cost-prohibitive for users. Suppressing RIN with BD-OCT provides faster imaging speeds and allows using less expensive, low repetition rate SC lasers, which makes techniques, such as vis-OCT, more practical for research and clinical uses.

Adaptive balance uses background intensity decay caused by RIN to generate a pixel-matching interpolation vector. Selecting pixels near the zero delay effectively serves as a low-pass filter to extract the balanced DC components. When the wavelengths of the subtracted interferograms are mismatched, the DC component of the balanced interferogram increases in amplitude and variance. Certain examples provide an adaptive balance method and associated system to automatically select interpolation vector coefficients that minimize or otherwise reduce the amplitude and variance of the DC term. Because adaptive balance selects interpolation vector coefficients based on the characteristics of the DC component, certain examples can be applied to any SD-OCT dataset regardless of RIN or signal level. As demonstrated by each test case shown in the figures, adaptive balance used with a spectrometer pair can achieve at least the same level of noise suppression as the control method that generated an interpolation vector from a RIN-dominated dataset.

Spectrometer camera gain level can influence the intensity of the detected interferogram before reaching the saturation level of the camera's digital to analog converter. Thus, with low camera gain, higher intensity can be recorded. At low camera gain, the reference arm power can be increased to its maximum level. Because RIN scales by a power of two of the incident power, spectrometer matching methods requiring RIN-dominated input perform better with low camera gain. However, when the camera gain is increased 16-fold, detector saturation can occur, which reduces the RIN amplitude relative to other noises. Notably, the adaptive balance methods and systems disclosed and described herein performed better than or comparable to pre-calibrated control methods regardless of amplification level, thus, providing a robust subpixel matching method without the need for pre-calibration.

In traditional SD-OCT systems using only one spectrometer, the effects of RIN can also be mitigated by increasing camera exposure time. Longer exposure time integrates more SC pulses for each A-line, which effectively increases the signal and lowers the RIN. Thus, for RIN-based spectrometer matching methods, the exposure time is reduced to a minimal value to capture the highest RIN amplitude possible. As illustrated by the results shown in the figures and described above, adaptive balance provides the most robust spectrometer matching method when the exposure time is varied.

Another solution for mitigating the effects of RIN in traditional SD-OCT systems is to use a high repetition rate SC laser. Increasing the repetition rate allows more SC pulses to be integrated for the same spectrometer camera exposure time. FIGS. 12A-12B compared balanced image quality using a 30-MHz and a 300-MHz laser. Like other tests, adaptive balance performed as well as the pre-calibrated control and better than the other subpixel matching methods regardless of the repetition rate. As such, adaptive balance is the most robust spectrometer matching approach when the light source repetition rate is varied.

As such, certain examples provide a robust framework and methodology for adaptive balance, which can select an optimal interpolation vector regardless of RIN or signal level. Adaptive balance can be readily implemented in any SD-BD-OCT setup. Thus, adaptive balance can be directly translated to any clinical SD-BD-OCT system, eliminating the need for routine recalibration. Further, adaptive balance can be applied in SD-BD-OCT systems where RIN does not dominate other noise sources.

Example Computing Platform

Figure 14:
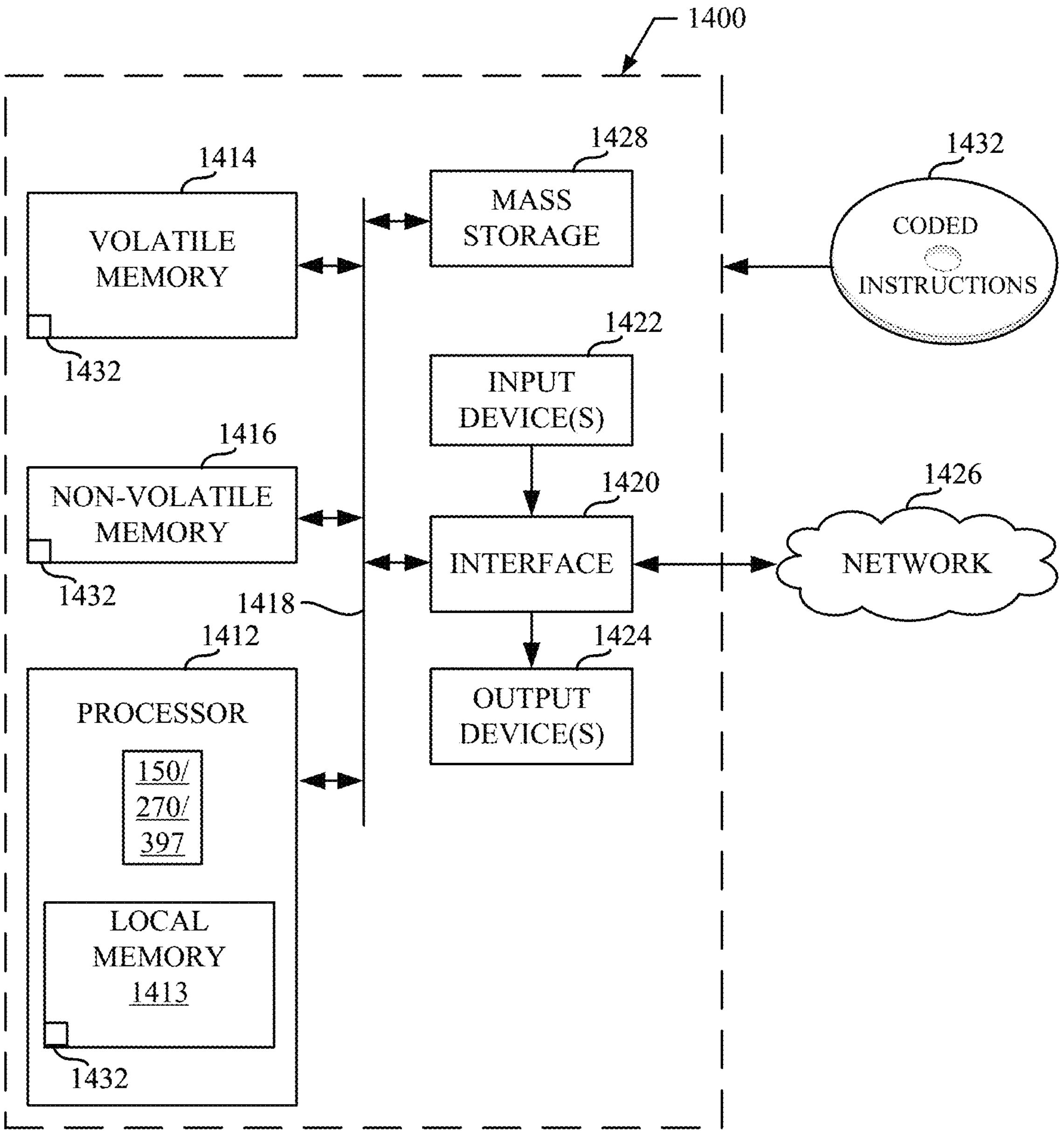
FIG. 14 depicts an example software and computer processor system on which the systems and methods described and disclosed herein can be implemented.

FIG. 14 is a block diagram of an example programmable circuitry platform 1400 structured to execute and/or instantiate the example machine-readable instructions and/or the example operations of FIGS. 7-8 to implement the example systems/apparatus of FIGS. 1-6. The programmable circuitry platform 1400 can be, for example, a server, a personal computer, a workstation, a self-learning machine (e.g., a neural network), a mobile device (e.g., a cell phone, a smart phone, a tablet such as an iPad™), a personal digital assistant (PDA), an Internet appliance, a headset (e.g., an augmented reality (AR) headset, a virtual reality (VR) headset, etc.) or other wearable device, or any other type of computing and/or electronic device.

The programmable circuitry platform 1400 of the illustrated example includes programmable circuitry 1412. The programmable circuitry 1412 of the illustrated example is hardware. For example, the programmable circuitry 1412 can be implemented by one or more integrated circuits, logic circuits, FPGAs, microprocessors, CPUs, GPUs, DSPs, and/or microcontrollers from any desired family or manufacturer. The programmable circuitry 1412 may be implemented by one or more semiconductor based (e.g., silicon based) devices. In this example, the programmable circuitry 1412 implements the processor 150, 270, and/or 397. The programmable circuitry 1412 of the illustrated example includes a local memory 1413 (e.g., a cache, registers, etc.). The programmable circuitry 1412 of the illustrated example is in communication with main memory 1414, 1416, which includes a volatile memory 1414 and a non-volatile memory 1416, by a bus 1418. The volatile memory 1414 may be implemented by Synchronous Dynamic Random Access Memory (SDRAM), Dynamic Random Access Memory (DRAM), RAMBUS® Dynamic Random Access Memory (RDRAM®), and/or any other type of RAM device. The non-volatile memory 1416 may be implemented by flash memory and/or any other desired type of memory device. Access to the main memory 1414, 1416 of the illustrated example is controlled by a memory controller 1417. In some examples, the memory controller 1417 may be implemented by one or more integrated circuits, logic circuits, microcontrollers from any desired family or manufacturer, or any other type of circuitry to manage the flow of data going to and from the main memory 1414, 1416.

The programmable circuitry platform 1400 of the illustrated example also includes interface circuitry 1420. The interface circuitry 1420 may be implemented by hardware in accordance with any type of interface standard, such as an Ethernet interface, a universal serial bus (USB) interface, a Bluetooth® interface, a near field communication (NFC) interface, a Peripheral Component Interconnect (PCI) interface, and/or a Peripheral Component Interconnect Express (PCIe) interface.

In the illustrated example, one or more input devices 1422 are connected to the interface circuitry 1420. The input device(s) 1422 permit(s) a user (e.g., a human user, a machine user, etc.) to enter data and/or commands into the programmable circuitry 1412. The input device(s) 1422 can be implemented by, for example, an audio sensor, a microphone, a camera (still or video), a keyboard, a button, a mouse, a touchscreen, a trackpad, a trackball, an isopoint device, and/or a voice recognition system.

One or more output devices 1424 are also connected to the interface circuitry 1420 of the illustrated example. The output device(s) 1424 can be implemented, for example, by display devices (e.g., a light emitting diode (LED), an organic light emitting diode (OLED), a liquid crystal display (LCD), a cathode ray tube (CRT) display, an in-place switching (IPS) display, a touchscreen, etc.), a tactile output device, a printer, and/or speaker. The interface circuitry 1420 of the illustrated example, thus, typically includes a graphics driver card, a graphics driver chip, and/or graphics processor circuitry such as a GPU.

The interface circuitry 1420 of the illustrated example also includes a communication device such as a transmitter, a receiver, a transceiver, a modem, a residential gateway, a wireless access point, and/or a network interface to facilitate exchange of data with external machines (e.g., computing devices of any kind) by a network 1426. The communication can be by, for example, an Ethernet connection, a digital subscriber line (DSL) connection, a telephone line connection, a coaxial cable system, a satellite system, a beyond-line-of-site wireless system, a line-of-site wireless system, a cellular telephone system, an optical connection, etc.

The programmable circuitry platform 1400 of the illustrated example also includes one or more mass storage discs or devices 1428 to store firmware, software, and/or data. Examples of such mass storage discs or devices 1428 include magnetic storage devices (e.g., floppy disk, drives, HDDs, etc.), optical storage devices (e.g., Blu-ray disks, CDs, DVDs, etc.), RAID systems, and/or solid-state storage discs or devices such as flash memory devices and/or SSDs.

The machine readable instructions 1432, which may be implemented by the machine readable instructions of FIGS. 7-8, may be stored in the mass storage device 1428, in the volatile memory 1414, in the non-volatile memory 1416, and/or on at least one non-transitory computer readable storage medium such as a CD or DVD which may be removable.

Figure 15:
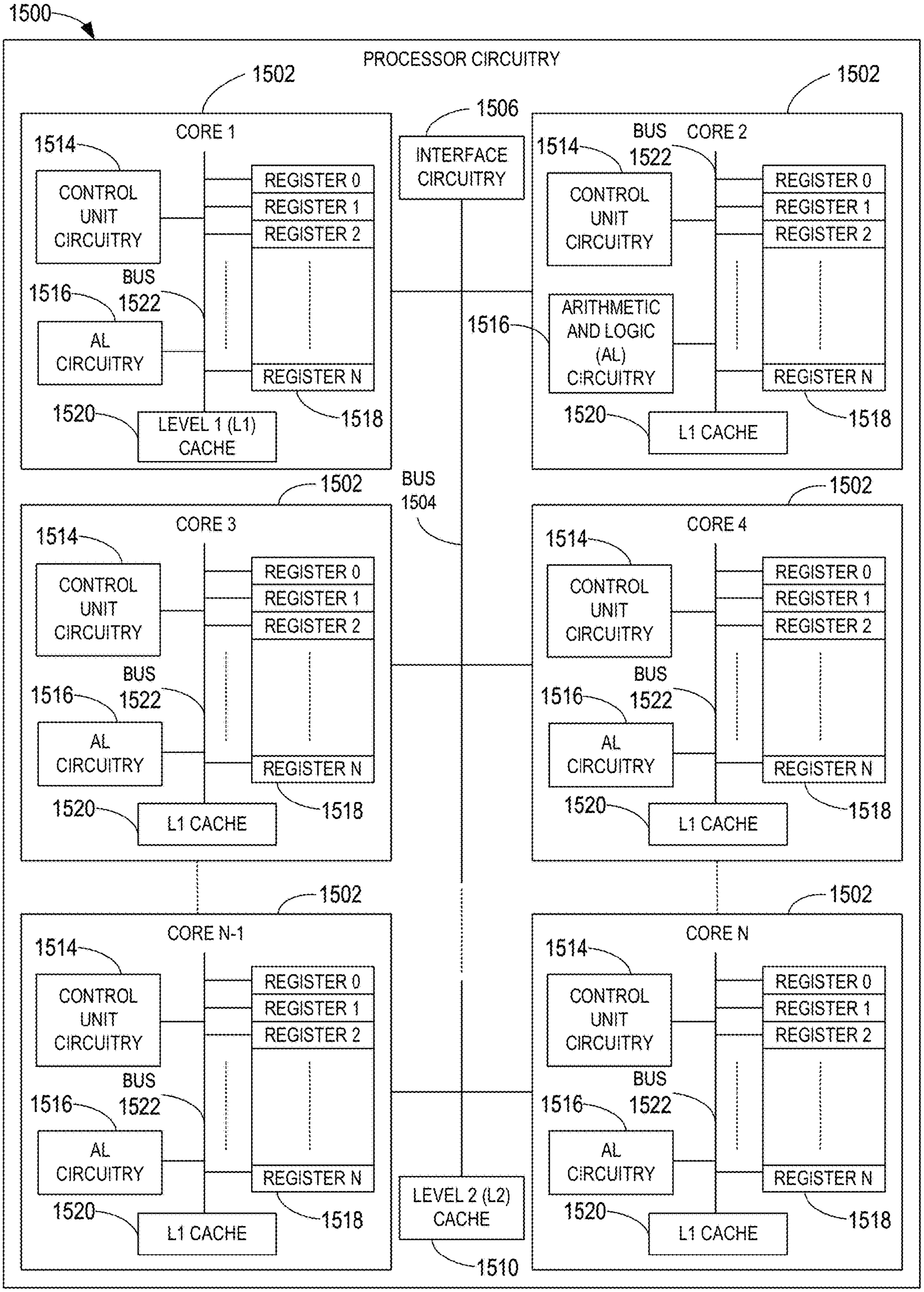
FIG. 15 depicts an example software and computer processor system on which the systems and methods described and disclosed herein can be implemented.

FIG. 15 is a block diagram of an example implementation of the programmable circuitry 1412 of FIG. 14. In this example, the programmable circuitry 1412 of FIG. 14 is implemented by a microprocessor 1500. For example, the microprocessor 1500 may be a general-purpose microprocessor (e.g., general-purpose microprocessor circuitry). The microprocessor 1500 executes some or all of the machine-readable instructions of the flowcharts of FIGS. 7-8 to effectively instantiate the circuitry of FIGS. 1-6 as logic circuits to perform operations corresponding to those machine readable instructions. In some such examples, the circuitry of FIGS. 1-6 is instantiated by the hardware circuits of the microprocessor 1500 in combination with the machine-readable instructions. For example, the microprocessor 1500 may be implemented by multi-core hardware circuitry such as a CPU, a DSP, a GPU, an XPU, etc. Although it may include any number of example cores 1502 (e.g., 1 core), the microprocessor 1500 of this example is a multi-core semiconductor device including N cores. The cores 1502 of the microprocessor 1500 may operate independently or may cooperate to execute machine readable instructions. For example, machine code corresponding to a firmware program, an embedded software program, or a software program may be executed by one of the cores 1502 or may be executed by multiple ones of the cores 1502 at the same or different times. In some examples, the machine code corresponding to the firmware program, the embedded software program, or the software program is split into threads and executed in parallel by two or more of the cores 1502. The software program may correspond to a portion or all of the machine readable instructions and/or operations represented by the flowcharts of FIGS. 7-8.

The cores 1502 may communicate by a first example bus 1504. In some examples, the first bus 1504 may be implemented by a communication bus to effectuate communication associated with one(s) of the cores 1502. For example, the first bus 1504 may be implemented by at least one of an Inter-Integrated Circuit (I2C) bus, a Serial Peripheral Interface (SPI) bus, a PCI bus, or a PCIe bus. Additionally or alternatively, the first bus 1504 may be implemented by any other type of computing or electrical bus. The cores 1502 may obtain data, instructions, and/or signals from one or more external devices by example interface circuitry 1506. The cores 1502 may output data, instructions, and/or signals to the one or more external devices by the interface circuitry 1506. Although the cores 1502 of this example include example local memory 1520 (e.g., Level 1 ($L_1$) cache that may be split into an $L_1$ data cache and an $L_1$ instruction cache), the microprocessor 1500 also includes example shared memory 1510 that may be shared by the cores (e.g., Level 2 ($L_2$ cache)) for high-speed access to data and/or instructions. Data and/or instructions may be transferred (e.g., shared) by writing to and/or reading from the shared memory 1510. The local memory 1520 of each of the cores 1502 and the shared memory 1510 may be part of a hierarchy of storage devices including multiple levels of cache memory and the main memory (e.g., the main memory 1414, 1416 of FIG. 14). Typically, higher levels of memory in the hierarchy exhibit lower access time and have smaller storage capacity than lower levels of memory. Changes in the various levels of the cache hierarchy are managed (e.g., coordinated) by a cache coherency policy.

Each core 1502 may be referred to as a CPU, DSP, GPU, etc., or any other type of hardware circuitry. Each core 1502 includes control unit circuitry 1514, arithmetic and logic (AL) circuitry (sometimes referred to as an ALU) 1516, a plurality of registers 1518, the local memory 1520, and a second example bus 1522. Other structures may be present. For example, each core 1502 may include vector unit circuitry, single instruction multiple data (SIMD) unit circuitry, load/store unit (LSU) circuitry, branch/jump unit circuitry, floating-point unit (FPU) circuitry, etc. The control unit circuitry 1514 includes semiconductor-based circuits structured to control (e.g., coordinate) data movement within the corresponding core 1502. The AL circuitry 1516 includes semiconductor-based circuits structured to perform one or more mathematic and/or logic operations on the data within the corresponding core 1502. The AL circuitry 1516 of some examples performs integer based operations. In other examples, the AL circuitry 1516 also performs floating-point operations. In yet other examples, the AL circuitry 1516 may include first AL circuitry that performs integer-based operations and second AL circuitry that performs floating-point operations. In some examples, the AL circuitry 1516 may be referred to as an Arithmetic Logic Unit (ALU).

The registers 1518 are semiconductor-based structures to store data and/or instructions such as results of one or more of the operations performed by the AL circuitry 1516 of the corresponding core 1502. For example, the registers 1518 may include vector register(s), SIMD register(s), general-purpose register(s), flag register(s), segment register(s), machine-specific register(s), instruction pointer register(s), control register(s), debug register(s), memory management register(s), machine check register(s), etc. The registers 1518 may be arranged in a bank as shown in FIG. 15. Alternatively, the registers 1518 may be organized in any other arrangement, format, or structure, such as by being distributed throughout the core 1502 to shorten access time. The second bus 1522 may be implemented by at least one of an I2C bus, a SPI bus, a PCI bus, or a PCIe bus.

Each core 1502 and/or, more generally, the microprocessor 1500 may include additional and/or alternate structures to those shown and described above. For example, one or more clock circuits, one or more power supplies, one or more power gates, one or more cache home agents (CHAs), one or more converged/common mesh stops (CMSs), one or more shifters (e.g., barrel shifter(s)) and/or other circuitry may be present. The microprocessor 1500 is a semiconductor device fabricated to include many transistors interconnected to implement the structures described above in one or more integrated circuits (ICs) contained in one or more packages.

The microprocessor 1500 may include and/or cooperate with one or more accelerators (e.g., acceleration circuitry, hardware accelerators, etc.). In some examples, accelerators are implemented by logic circuitry to perform certain tasks more quickly and/or efficiently than can be done by a general-purpose processor. Examples of accelerators include ASICs and FPGAs such as those discussed herein. A GPU, DSP and/or other programmable device can also be an accelerator. Accelerators may be on-board the microprocessor 1500, in the same chip package as the microprocessor 1500 and/or in one or more separate packages from the microprocessor 1500.

Figure 16:
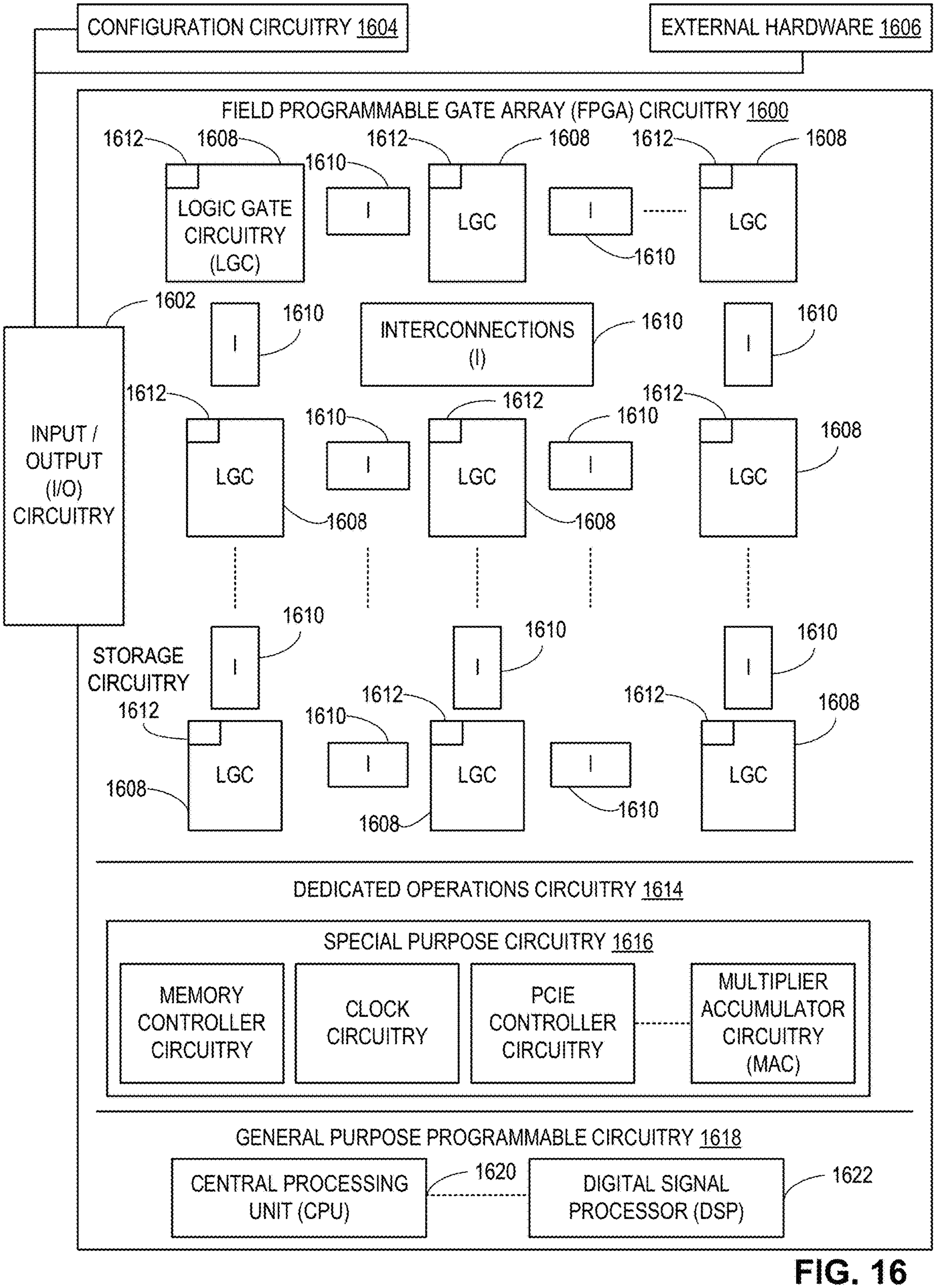
FIG. 16 depicts an example software and computer processor system on which the systems and methods described and disclosed herein can be implemented.

FIG. 16 is a block diagram of another example implementation of the programmable circuitry 1412 of FIG. 14. In this example, the programmable circuitry 1412 is implemented by FPGA circuitry 1600. For example, the FPGA circuitry 1600 may be implemented by an FPGA. The FPGA circuitry 1600 can be used, for example, to perform operations that could otherwise be performed by the example microprocessor 1500 of FIG. 15 executing corresponding machine readable instructions. However, once configured, the FPGA circuitry 1600 instantiates the operations and/or functions corresponding to the machine readable instructions in hardware and, thus, can often execute the operations/functions faster than they could be performed by a general-purpose microprocessor executing the corresponding software.

More specifically, in contrast to the microprocessor 1500 of FIG. 15 described above (which is a general purpose device that may be programmed to execute some or all of the machine readable instructions represented by the flowchart (s) of FIGS. 7-8 but whose interconnections and logic circuitry are fixed once fabricated), the FPGA circuitry 1600 of the example of FIG. 16 includes interconnections and logic circuitry that may be configured, structured, programmed, and/or interconnected in different ways after fabrication to instantiate, for example, some or all of the operations/functions corresponding to the machine readable instructions represented by the flowchart(s) of FIGS. 7-8. In particular, the FPGA circuitry 1600 may be thought of as an array of logic gates, interconnections, and switches. The switches can be programmed to change how the logic gates are interconnected by the interconnections, effectively forming one or more dedicated logic circuits (unless and until the FPGA circuitry 1600 is reprogrammed). The configured logic circuits enable the logic gates to cooperate in different ways to perform different operations on data received by input circuitry. Those operations may correspond to some or all of the instructions (e.g., the software and/or firmware) represented by the flowchart(s) of FIGS. 7-8. As such, the FPGA circuitry 1600 may be configured and/or structured to effectively instantiate some or all of the operations/functions corresponding to the machine readable instructions of the flowchart(s) of FIGS. 7-8 as dedicated logic circuits to perform the operations/functions corresponding to those software instructions in a dedicated manner analogous to an ASIC. Therefore, the FPGA circuitry 1600 may perform the operations/functions corresponding to the some or all of the machine readable instructions of FIGS. 7-8 faster than the general-purpose microprocessor can execute the same.

In the example of FIG. 16, the FPGA circuitry 1600 is configured and/or structured in response to being programmed (and/or reprogrammed one or more times) based on a binary file. In some examples, the binary file may be compiled and/or generated based on instructions in a hardware description language (HDL) such as Lucid, Very High Speed Integrated Circuits (VHSIC) Hardware Description Language (VHDL), or Verilog. For example, a user (e.g., a human user, a machine user, etc.) may write code or a program corresponding to one or more operations/functions in an HDL; the code/program may be translated into a low-level language as needed; and the code/program (e.g., the code/program in the low-level language) may be converted (e.g., by a compiler, a software application, etc.) into the binary file. In some examples, the FPGA circuitry 1600 of FIG. 16 may access and/or load the binary file to cause the FPGA circuitry 1600 of FIG. 16 to be configured and/or structured to perform the one or more operations/functions. For example, the binary file may be implemented by a bit stream (e.g., one or more computer-readable bits, one or more machine-readable bits, etc.), data (e.g., computer-readable data, machine-readable data, etc.), and/or machine-readable instructions accessible to the FPGA circuitry 1600 of FIG. 16 to cause configuration and/or structuring of the FPGA circuitry 1600 of FIG. 16, or portion(s) thereof.

In some examples, the binary file is compiled, generated, transformed, and/or otherwise output from a uniform software platform utilized to program FPGAs. For example, the uniform software platform may translate first instructions (e.g., code or a program) that correspond to one or more operations/functions in a high-level language (e.g., C, C++, Python, etc.) into second instructions that correspond to the one or more operations/functions in an HDL. In some such examples, the binary file is compiled, generated, and/or otherwise output from the uniform software platform based on the second instructions. In some examples, the FPGA circuitry 1600 of FIG. 16 may access and/or load the binary file to cause the FPGA circuitry 1600 of FIG. 16 to be configured and/or structured to perform the one or more operations/functions. For example, the binary file may be implemented by a bit stream (e.g., one or more computer-readable bits, one or more machine-readable bits, etc.), data (e.g., computer-readable data, machine-readable data, etc.), and/or machine-readable instructions accessible to the FPGA circuitry 1600 of FIG. 16 to cause configuration and/or structuring of the FPGA circuitry 1600 of FIG. 16, or portion(s) thereof.

The FPGA circuitry 1600 of FIG. 16, includes example input/output (I/O) circuitry 1602 to obtain and/or output data to/from example configuration circuitry 1604 and/or external hardware 1606. For example, the configuration circuitry 1604 may be implemented by interface circuitry that may obtain a binary file, which may be implemented by a bit stream, data, and/or machine-readable instructions, to configure the FPGA circuitry 1600, or portion(s) thereof. In some such examples, the configuration circuitry 1604 may obtain the binary file from a user, a machine (e.g., hardware circuitry (e.g., programmable or dedicated circuitry) that may implement an Artificial Intelligence/Machine Learning (AI/ML) model to generate the binary file), etc., and/or any combination(s) thereof). In some examples, the external hardware 1606 may be implemented by external hardware circuitry. For example, the external hardware 1606 may be implemented by the microprocessor 1500 of FIG. 15.

The FPGA circuitry 1600 also includes an array of example logic gate circuitry 1608, a plurality of example configurable interconnections 1610, and example storage circuitry 1612. The logic gate circuitry 1608 and the configurable interconnections 1610 are configurable to instantiate one or more operations/functions that may correspond to at least some of the machine readable instructions of FIGS. 7-8 and/or other desired operations. The logic gate circuitry 1608 shown in FIG. 16 is fabricated in blocks or groups. Each block includes semiconductor-based electrical structures that may be configured into logic circuits. In some examples, the electrical structures include logic gates (e.g., And gates, Or gates, Nor gates, etc.) that provide basic building blocks for logic circuits. Electrically controllable switches (e.g., transistors) are present within each of the logic gate circuitry 1608 to enable configuration of the electrical structures and/or the logic gates to form circuits to perform desired operations/functions. The logic gate circuitry 1608 may include other electrical structures such as look-up tables (LUTs), registers (e.g., flip-flops or latches), multiplexers, etc.

The configurable interconnections 1610 of the illustrated example are conductive pathways, traces, vias, or the like that may include electrically controllable switches (e.g., transistors) whose state can be changed by programming (e.g., using an HDL instruction language) to activate or deactivate one or more connections between one or more of the logic gate circuitry 1608 to program desired logic circuits.

The storage circuitry 1612 of the illustrated example is structured to store result(s) of the one or more of the operations performed by corresponding logic gates. The storage circuitry 1612 may be implemented by registers or the like. In the illustrated example, the storage circuitry 1612 is distributed amongst the logic gate circuitry 1608 to facilitate access and increase execution speed.

The example FPGA circuitry 1600 of FIG. 16 also includes example dedicated operations circuitry 1614. In this example, the dedicated operations circuitry 1614 includes special purpose circuitry 1616 that may be invoked to implement commonly used functions to avoid the need to program those functions in the field. Examples of such special purpose circuitry 1616 include memory (e.g., DRAM) controller circuitry, PCIe controller circuitry, clock circuitry, transceiver circuitry, memory, and multiplier-accumulator circuitry. Other types of special purpose circuitry may be present. In some examples, the FPGA circuitry 1600 may also include example general purpose programmable circuitry 1618 such as an example CPU 1620 and/or an example DSP 1622. Other general purpose programmable circuitry 1618 may additionally or alternatively be present such as a GPU, an XPU, etc., that can be programmed to perform other operations.

Although FIGS. 15 and 16 illustrate two example implementations of the programmable circuitry 1412 of FIG. 14, many other approaches are contemplated. For example, FPGA circuitry may include an on-board CPU, such as one or more of the example CPU 1620 of FIG. 15. Therefore, the programmable circuitry 1412 of FIG. 14 may additionally be implemented by combining at least the example microprocessor 1500 of FIG. 15 and the example FPGA circuitry 1600 of FIG. 16. In some such hybrid examples, one or more cores 1502 of FIG. 15 may execute a first portion of the machine readable instructions represented by the flowchart(s) of FIGS. 7-8 to perform first operation(s)/function(s), the FPGA circuitry 1600 of FIG. 16 may be configured and/or structured to perform second operation(s)/function(s) corresponding to a second portion of the machine readable instructions represented by the flowcharts of FIG. [Flowcharts], and/or an ASIC may be configured and/or structured to perform third operation(s)/function(s) corresponding to a third portion of the machine readable instructions represented by the flowcharts of FIGS. 7-8.

It should be understood that some or all of the circuitry of FIGS. 1-6 may, thus, be instantiated at the same or different times. For example, same and/or different portion(s) of the microprocessor 1500 of FIG. 15 may be programmed to execute portion(s) of machine-readable instructions at the same and/or different times. In some examples, same and/or different portion(s) of the FPGA circuitry 1600 of FIG. 16 may be configured and/or structured to perform operations/functions corresponding to portion(s) of machine-readable instructions at the same and/or different times.

In some examples, some or all of the circuitry of FIGS. 1-6 may be instantiated, for example, in one or more threads executing concurrently and/or in series. For example, the microprocessor 1500 of FIG. 15 may execute machine readable instructions in one or more threads executing concurrently and/or in series. In some examples, the FPGA circuitry 1600 of FIG. 16 may be configured and/or structured to carry out operations/functions concurrently and/or in series. Moreover, in some examples, some or all of the circuitry of FIGS. 1-6 may be implemented within one or more virtual machines and/or containers executing on the microprocessor 1500 of FIG. 15.

In some examples, the programmable circuitry 1412 of FIG. 14 may be in one or more packages. For example, the microprocessor 1500 of FIG. 15 and/or the FPGA circuitry 1600 of FIG. 16 may be in one or more packages. In some examples, an XPU may be implemented by the programmable circuitry 1412 of FIG. 14, which may be in one or more packages. For example, the XPU may include a CPU (e.g., the microprocessor 1500 of FIG. 15, the CPU 1620 of FIG. 16, etc.) in one package, a DSP (e.g., the DSP 1622 of FIG. 16) in another package, a GPU in yet another package, and an FPGA (e.g., the FPGA circuitry 1600 of FIG. 16) in still yet another package.

From the foregoing, it will be appreciated that example systems, apparatus, articles of manufacture, and methods have been disclosed that improve OCT imaging by reducing noise through acquisition of image data using two photodetectors. Disclosed systems, apparatus, articles of manufacture, and methods improve the efficiency of using a computing device by adaptive balancing output provided by the pair of photodetectors to reduce noise in an ocular image without need for separate calibration. Disclosed systems, apparatus, articles of manufacture, and methods are accordingly directed to one or more improvement(s) in the operation of a machine such as a computer or other electronic and/or mechanical device.

Example methods, apparatus, systems, and articles of manufacture to reduce or remove noise in an ocular image through adaptive balancing are disclosed herein. Further examples and combinations thereof include the following:

Example 1 includes an optical coherence tomography (OCT) imaging system, the system including: a light source to generate a beam of radiation; a first photodetector to acquire first data with respect to the beam of radiation; a second photodetector to acquire second data with respect to the beam of radiation; a coupler to direct a first portion of the beam to a sample arm and to direct a second portion of the beam to a reference arm, the coupler to combine first light from the sample arm and second light from the reference arm to form combined light, the combined light to be split into a first portion to be detected by the first photodetector to form the first data and a second portion to be detected by the second photodetector to form the second data; and processor circuitry to generate a first noise profile of the first data and a second noise profile of the second data, the processor to compare the first noise profile and the second noise profile, the processor to generate an image using the first data, the second data, and the comparison of the first noise profile and the second noise profile, the processor to store the image for at least one of analysis or deployment.

Example 2 includes the system of any preceding clause, wherein the light source is at least one of a laser, a wideband light source, a lamp, or a light-emitting diode (LED).

Example 3 includes the system of any preceding clause, wherein at least one of the first photodetector or the second photodetector is a spectrometer.

Example 4 includes the system of any preceding clause, wherein the first photodetector acquires the first portion of the combined light and the second photodetector independently acquires the second portion of the combined light.

Example 5 includes the system of any preceding clause, wherein the combined light has an interference with contribution from the sample arm and the reference arm.

Example 6 includes the system of any preceding clause, wherein the combined light contains noise.

Example 7 includes the system of any preceding clause, wherein the first noise profile represents a first interference fringe and wherein the second noise profile represents a second interference fringe.

Example 8 includes the system of any preceding clause, wherein the processor circuitry is to apply an interpolation vector to the second noise profile to align the second noise profile with the first noise profile.

Example 9 includes the system of any preceding clause, wherein the processor circuitry is to subtract the aligned second noise profile from the first noise profile to determine a difference.

Example 10 includes the system of any preceding clause, wherein the processor circuitry is to: resample using the difference; correct dispersion; perform a linear transform; and output the image.

Example 11 includes the system of any preceding clause, wherein the linear transform includes a Fourier transform.

Example 12 includes the system of any preceding clause, wherein the processor circuitry is to generate a calibration map from noise remaining after the linear transform.

Example 13 includes the system of any preceding clause, wherein the interpolation vector is generated by iterating a first order polynomial and a second order polynomial with coefficients, A-line reconstruction, and reduction in a DC term.

Example 14 includes the system of any preceding clause, wherein the processor circuitry is to reduce an intensity of the light source to a threshold value.

Example 15 includes the system of any preceding clause, wherein the coupler includes fiber optics.

Example 16 includes the system of any preceding clause, wherein the processor circuitry applies a spectral filter to compare the first noise profile and the second noise profile.

Example 17 includes the system of any preceding clause, wherein the first photodetector and the second photodetector are combined in a single unit.

Example 18 is a non-transitory computer-readable storage medium including instructions that, when executed, cause processor circuitry to at least: generate a first noise profile from a first portion of data received in combination from a sample arm and a reference arm, the first portion received by a first photodetector; generate a second noise profile from a second portion of data received in combination from the sample arm and the reference arm, the second portion received by a second photodetector; compare the first noise profile and the second noise profile; generate an image using the first portion of data, the second portion of data, and the comparison of the first noise profile and the second noise profile; and output the image for at least one of analysis or deployment.

Example 19 includes the non-transitory computer-readable storage medium of any preceding clause, wherein the instructions, when executed, cause the processor circuitry to: apply an interpolation vector to the second noise profile to align the second noise profile with the first noise profile; and subtract the aligned second noise profile from the first noise profile to determine a difference.

Example 20 includes the non-transitory computer-readable storage medium of any preceding clause, wherein the instructions, when executed, cause the processor circuitry to: resample using the difference; correct dispersion; perform a linear transform; and output the image.

Example 21 is an apparatus including means for generating a first noise profile from a first portion of data received in combination from a sample arm and a reference arm, the first portion received by a first photodetector and for generating a second noise profile from a second portion of data received in combination from the sample arm and the reference arm, the second portion received by a second photodetector; means for comparing the first noise profile and the second noise profile; means for generate an image using the first portion of data, the second portion of data, and the comparison of the first noise profile and the second noise profile; and means for outputting the image for at least one of analysis or deployment.

Example 22 includes the apparatus of any preceding clause, wherein the means for generating a first noise profile and a second noise profile includes a first means for generating the first noise profile and a second means for generating the second noise profile.

Example 23 includes the system of any preceding clause, wherein the image is generated using optical coherence tomography methods.

Example 24 includes the system of any preceding clause, wherein the first or second photodetector is a spectrometer.

Example 25 includes the system of any preceding clause, wherein the first photodetector acquires the first portion combined light and the second photodetector independently acquires the second portion of the combine light.

Example 26 includes the system of any preceding clause, wherein the combined light has an interference with contribution from the sample and reference arms.

Example 27 includes the system of any preceding clause, wherein the combined light does not have an interference with contribution from the sample and reference arms and only contains noises.

Example 28 includes the system of any preceding clause, wherein the combined light does not have an interference with contribution from the sample and reference arms and only contains light from the light source.

Example 29 includes the system of any preceding clause, wherein the acquisitions by the two photodetectors are synchronized.

Example 30 includes the system of any preceding clause, wherein the first photodetector and the second photodetector independently acquires with respective two portions of the light.

Example 31 includes the system of any preceding clause, wherein a means to measure the noise profile further includes any measurement of a relationship established mathematically to correlate the noise signals independently acquired from the first photodetector and the second photodetector.

Example 32 includes the system of any preceding clause, wherein a mathematical correlation is applied to the signals acquired by the first photodetector and mapped to the second photodetector before the linear transform is applied.

Example 33 includes the system of any preceding clause, wherein the photodetectors acquire the spectra of the noises.

Example 34 includes the system of any preceding clause, wherein the linear transform contains a Fourier transform.

Example 35 includes the system of any preceding clause, wherein a means to measure and compare the noise profile further includes reducing the intensity of the light source to a threshold value such that the signal acquired from the first photodetector or second photodetector is at least 10% noise signal.

Example 36 includes the system of any preceding clause, wherein the means to measure and compare the noise profile further includes reducing the intensity of the light source to a threshold value such that the signal acquired from the first photodetector or second photodetector is at least 20% noise signal.

Example 37 includes the system of any preceding clause, wherein the means to measure and compare the noise profile further includes reducing the intensity of the light source to a threshold value such that the signal acquired from the first photodetector or second photodetector is at least 30% noise signal.

Example 38 includes the system of any preceding clause, wherein the means to measure and compare the noise profile further includes reducing the intensity of the light source to a threshold value such that the signal acquired from the first photodetector or second photodetector is at least 40% noise signal.

Example 39 includes the system of any preceding clause, wherein the means to measure and compare the noise profile further includes reducing the intensity of the light source to a threshold value such that the signal acquired from the first photodetector or second photodetector is at least 50% noise signal.

Example 40 includes the system of any preceding clause, wherein the means to measure and compare the noise profile further includes reducing the intensity of the light source to a threshold value such that the signal acquired from the first photodetector or second photodetector is at least 60% noise signal.

Example 41 includes the system of any preceding clause, wherein the means to measure and compare the noise profile further includes reducing the intensity of the light source to a threshold value such that the signal acquired from the first photodetector or second photodetector is at least 70% noise signal.

Example 42 includes the system of any preceding clause, wherein the means to measure and compare the noise profile further includes reducing the intensity of the light source to a threshold value such that the signal acquired from the first photodetector or second photodetector is at least 80% noise signal.

Example 43 includes the system of any preceding clause, wherein the means to measure and compare the noise profile further includes reducing the intensity of the light source to a threshold value such that the signal acquired from the first photodetector or second photodetector is at least 90% noise signal.

Example 44 includes the system of any preceding clause, wherein the means to measure and compare the noise profile further includes reducing the intensity of the light source to a threshold value such that the signal acquired from the first photodetector, or second photodetector is at least 95% noise signal.

Example 45 includes the system of any preceding clause, wherein the means to measure and compare the noise profile further includes reducing the intensity of the light source to a threshold value such that the signal acquired from the first photodetector, or second photodetector is at least 99% noise signal.

Example 46 includes the system of any preceding clause, wherein the means to measure and compare the noise profile further includes generating a calibration map between the first photodetector and the second photodetector, matching and identifying constant elements in the calibration map, and subtracting the constant elements from the signal used to generate the image.

Example 47 includes the system of any preceding clause, wherein the calibrated mapping between the first photodetector and the second photodetector is based on the pixel element equal to the element of the spectrometer.

Example 48 includes the system of any preceding clause, wherein the calibrated mapping between the first photodetector and the second photodetector is based on the sub pixel element smaller than the element of the spectrometer.

Example 49 includes the system of any preceding clause, wherein the combination of the constant elements from the signal used to generate the image is noise reduction.

Example 50 includes the system of any preceding clause, wherein the mathematical correlation of the constant elements from the signal used to generate the image is a sub-pixel correction.

Example 51 includes the system of any preceding clause, wherein the mathematical correlation of the constant elements from the signal used to generate the image is at a resolution of less than one pixel for either the first photodetector or the second photodetector.

Example 52 includes the system of any preceding clause, wherein the generating a calibration map based on the mathematical correlation further includes generating a calibration map for one or more image acquisitions.

Example 53 includes the system of any preceding clause, wherein a calibration map is generated from the noise part of the signal after linear transform.

Example 54 includes the system of any preceding clause, wherein the calibration map generated from the image is approximated as a polynomial function of the constant detector elements.

Example 55 includes the system of any preceding clause, wherein the coefficients of the polynomial function characterize the offset and spacing between constant detector elements.

Example 56 includes the system of any preceding clause, wherein the coefficients are modified by computational optimization.

Example 57 includes the system of any preceding clause, wherein the computational optimization changes coefficients to minimize a cost function.

Example 58 includes the system of any preceding clause, wherein the cost function is a measure of the average intensity and noise profile of the image from a selected depth or whole image.

Example 59 includes the system of any preceding clause, wherein the means to measure and compare the noise profile of the first photodetector and the second photodetector is performed before the generation of an image.

Example 60 includes the system of any preceding clause, wherein the means to measure and compare the noise profile of the first photodetector and the second photodetector is performed to the generation of an image.

Example 61 includes the system of any preceding clause, wherein the means to measure and compare the noise profile of the first photodetector and the second photodetector is performed after the generation of an image.

Example 62 includes the system of any preceding clause, wherein the means to measure and compare the noise profile of the first photodetector and the second photodetector is performed simultaneously to the generation of an image.

Example 63 includes the system of any preceding clause, wherein the means to measure and compare the noise profile of the first photodetector and the second photodetector further includes matching the bandwidth of the first photodetector with the bandwidth of the second photodetector and shifting the pixels in each of the first and second photodetectors from left to right and nonlinear stretching/shrinking of the pixels in each of the first and second photodetectors.

Example 64 includes the system of any preceding clause, wherein the means to measure and compare the noise profile of the first photodetector and the second photodetector further includes linear or non-linear matching.

Example 65 includes the system of any preceding clause, wherein the means to measure and compare the noise profile of first photodetector and second photodetector further includes measurement of intrinsic or extrinsic noise signals.

Example 66 includes the system of any preceding clause, wherein the intrinsic noise signals further include any signal contribution from the light source or components of the system.

Example 67 includes the system of any preceding clause, wherein the extrinsic noise signals further include any noise signals contributed from signals externally applied to the system.

Example 68 includes the system of any preceding clause, wherein the noise signals include fluctuations in signal.

Example 69 includes the system of any preceding clause, wherein the, wherein the beam splitter and optics functioning to direct and combine light are single mode or multimode fiber optics.

Example 70 includes the system of any preceding clause, wherein the beam splitter and optics functioning to direct and combine light are a combination of bulk optics and single mode or multimode fiber optics.

Example 71 includes the system of any preceding clause, wherein the means to measure and compare the noise profile of the first photodetector and the second photodetector is achieved through the use of a spectral filter.

Example 72 includes the system of any preceding clause, wherein the two photodetectors can be either two independent units or be combined into a single unit as shown in FIG. 5.

Example 73 includes the system of any preceding clause, wherein the image used to measure and compare the noise profile of the first photodetector and the second photodetector can be acquired from a human eye.

Example 74 includes the system of any preceding clause, wherein the image used to measure and compare the noise profile of the first photodetector and the second photodetector can be acquired from an artificial sample.

Example 75 includes the system of any preceding clause, wherein the canceling of the noises between the first photodetector and the second photodetector can be performed each time before a human eye is image.

Example 76 includes the system of any preceding clause, wherein the canceling of the noises between the first photodetector and the second photodetector can be performed at any time when the system is not imaging a human eye.

What is claimed is:

1. An optical coherence tomography (OCT) imaging system, the system comprising:

a light source to generate a beam of radiation;

a first photodetector to acquire first data with respect to the beam of radiation;

a second photodetector to acquire second data with respect to the beam of radiation;

a beam splitter to direct a first portion of the beam to a sample arm and to direct a second portion of the beam to a reference arm, the beam splitter to combine first light from the sample arm and second light from the reference arm to form combined light, the combined light to be split into a third portion to be detected by the first photodetector to form the first data and fourth portion to be detected by the second photodetector to form the second data; and processor circuitry to generate a first noise profile of the first data and a second noise profile of the second data, the processor to compare the first noise profile and the second noise profile, the processor to generate an image using the first data, the second data, and the comparison of the first noise profile and the second noise profile, the processor to store the image for at least one of analysis or deployment, wherein the processor circuitry is to apply an interpolation vector to the second noise profile to align the second noise profile with the first noise profile, the interpolation vector generated by:

initializing the interpolation vector as an initial interpolation vector with a set of first-order coefficients;

iteratively updating the first-order coefficients of interpolation vector until a direct current component is reduced with respect to a threshold;

updating the interpolation vector with second-order coefficients to form a final interpolation vector; and reconstructing a balanced OCT A-line using the final interpolation vector, the A-line forming part of the image.

2. The system of claim 1, wherein the light source is at least one of a laser, a wideband light source, a wideband spatially coherent light source, a supercontinuum laser light source, a lamp, a superluminescent diode (SLD), an amplified spontaneous emission (ASE) light source, or a light-emitting diode (LED).

3. The system of claim 1, wherein at least one of the first photodetector or the second photodetector is a spectrometer.

4. The system of claim 1, wherein the first photodetector acquires the third first portion of the combined light and the second photodetector independently acquires the fourth second portion of the combined light.

5. The system of claim 1, wherein the third first portion and the fourth second portion have an interference with contribution from the sample arm and the reference arm.

6. The system of claim 1, wherein the first noise profile represents a first interference fringe and wherein the second noise profile represents a second interference fringe.

7. The system of claim 1, wherein the processor circuitry is to subtract the aligned second noise profile from the first noise profile to determine a difference.

8. The system of claim 7, wherein the processor circuitry is to:

resample using the difference;

correct dispersion;

perform a linear transform; and output the image.

9. The system of claim 8, wherein the linear transform includes a Fourier transform.

10. The system of claim 8, wherein the processor circuitry is to generate a calibration map from noise remaining after the linear transform.

11. The system of claim 1, wherein the interpolation vector is generated by iterating a first order polynomial and a second order polynomial with coefficients, A-line reconstruction, and reduction in a DC term.

12. The system of claim 1, wherein the processor circuitry is to reduce an intensity of the light source to a threshold value.

13. The system of claim 1, further including a fiber-based coupler.

14. The system of claim 1, wherein the processor circuitry applies a spectral filter to compare the first noise profile and the second noise profile.

15. The system of claim 1, wherein the first photodetector and the second photodetector are combined in a single unit.

16. The system of claim 1, wherein the interpolation vector is generated from at least one of noise-dominated data or a signal-dominated data.

17. A non-transitory computer-readable storage medium comprising instructions that, when executed, cause processor circuitry to at least:

generate a first noise profile from a first portion of data received in combination from a sample arm and a reference arm, the first portion received by a first photodetector;

generate a second noise profile from a second portion of data received in combination from the sample arm and the reference arm, the second portion received by a second photodetector;

compare the first noise profile and the second noise profile;

generate an image using the first portion of data, the second portion of data, and the comparison of the first noise profile and the second noise profile; and output the image for at least one of analysis or deployment, wherein the processor circuitry is to apply an interpolation vector to the second noise profile to align the second noise profile with the first noise profile, the interpolation vector generated by:

initializing the interpolation vector as an initial interpolation vector with a set of first-order coefficients;

iteratively updating the first-order coefficients of interpolation vector until a direct current component is reduced with respect to a threshold;

updating the interpolation vector with second-order coefficients to form a final interpolation vector; and reconstructing a balanced OCT A-line using the final interpolation vector, the A-line forming part of the image.

18. The non-transitory computer-readable storage medium of claim 17, wherein the instructions, when executed, cause the processor circuitry to:

subtract the aligned second noise profile from the first noise profile to determine a difference.

19. The non-transitory computer-readable storage medium of claim 18, wherein the instructions, when executed, cause the processor circuitry to:

resample using the difference;

correct dispersion;

perform a linear transform; and output the image.

* * * * *